(12) United States Patent
Zhang et al.

(10) Patent No.: US 10,632,070 B2
(45) Date of Patent: Apr. 28, 2020

(54) HYDROGEL TOXIN-ABSORBING OR BINDING NANOPARTICLES

(71) Applicant: The Regents of the University of California, Oakland, CA (US)

(72) Inventors: Liangfang Zhang, San Diego, CA (US); Che-Ming Jack Hu, San Diego, CA (US); Weiwei Gao, La Jolla, CA (US); Jonathan Coop, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/139,612

(22) Filed: Sep. 24, 2018

(65) Prior Publication Data
US 2019/0142746 A1 May 16, 2019

Related U.S. Application Data

(62) Division of application No. 15/126,342, filed as application No. PCT/US2015/021702 on Mar. 20, 2015, now Pat. No. 10,098,839.
(Continued)

(51) Int. Cl.
*A61K 9/06* (2006.01)
*A61K 9/16* (2006.01)
(Continued)

(52) U.S. Cl.
CPC .............. *A61K 9/06* (2013.01); *A61K 9/0019* (2013.01); *A61K 9/1629* (2013.01);
(Continued)

(58) Field of Classification Search
CPC ...... A61K 9/06; A61K 9/1629; A61K 9/5153; A61K 35/17; A61K 35/18; A61K 35/19;
(Continued)

(56) References Cited

U.S. PATENT DOCUMENTS 5,358,722 A 10/1994 Monzyk
5,491,219 A 2/1996 Mann
(Continued)

FOREIGN PATENT DOCUMENTS

CN 1798548 A 7/2006
CN 101306196 A 11/2008
(Continued)

OTHER PUBLICATIONS

Hu, et al., "Erythrocyte Membrane-Camouflaged Polymeric Nanoparticles as a Biomimetic Delivery Platform," PNAS, 2011, 10 8(27): 10980-10985.
(Continued)

*Primary Examiner* — Carlos A Azpuru
(74) *Attorney, Agent, or Firm* — Eversheds Sutherland (US) LLP

(57) ABSTRACT

The present invention provides for compositions comprising a polymeric hydrogel impregnated with a toxin-absorbing or binding nanoparticle. The present invention also provides for the use of the above compositions for decreasing or neutralizing the effect of a toxin, or for treating or preventing an infection by a microbe that produces a toxin, in a subject. The exemplary toxin is a biological toxin such as a viral, bacterial, fungal, plant or animal toxin.

33 Claims, 9 Drawing Sheets

Related U.S. Application Data

(60) Provisional application No. 61/955,962, filed on Mar. 20, 2014.

(51) Int. Cl.

| | | |
|---|---|---|
| A61K 9/51 | (2006.01) | |
| A61K 38/17 | (2006.01) | |
| A61K 35/17 | (2015.01) | |
| A61K 35/18 | (2015.01) | |
| A61K 35/19 | (2015.01) | |
| A61K 35/58 | (2015.01) | |
| A61K 35/63 | (2015.01) | |
| A61K 45/06 | (2006.01) | |
| A61K 31/49 | (2006.01) | |
| A61L 26/00 | (2006.01) | |
| A61K 9/00 | (2006.01) | |
| A61L 27/52 | (2006.01) | |
| A61L 27/54 | (2006.01) | |
| A61K 9/50 | (2006.01) | |

(52) U.S. Cl.
CPC .......... *A61K 9/5115* (2013.01); *A61K 9/5153* (2013.01); *A61K 9/5176* (2013.01); *A61K 31/49* (2013.01); *A61K 35/17* (2013.01); *A61K 35/18* (2013.01); *A61K 35/19* (2013.01); *A61K 35/58* (2013.01); *A61K 35/63* (2015.01); *A61K 38/1709* (2013.01); *A61K 45/06* (2013.01); *A61L 26/008* (2013.01); *A61L 27/52* (2013.01); *A61L 27/54* (2013.01); *A61K 9/5068* (2013.01); *A61L 2300/404* (2013.01); *A61L 2400/12* (2013.01); *Y02A 50/473* (2018.01)

(58) Field of Classification Search
CPC ......... A61K 35/58; A61K 35/63; A61L 27/52; A61L 27/54
See application file for complete search history.

(56) References Cited

U.S. PATENT DOCUMENTS

| | | | |
|---|---|---|---|
| 5,653,999 | A | 8/1997 | Gaudreault et al. |
| 6,361,797 | B1 | 3/2002 | Kuzma et al. |
| 8,846,026 | B2 | 9/2014 | Plebanski |
| 2004/0110695 | A1 | 6/2004 | Dobbie |
| 2004/0180094 | A1 | 9/2004 | Joyce |
| 2005/0118275 | A1 | 6/2005 | O'Hagan |
| 2005/0255152 | A1 | 11/2005 | Edwards et al. |
| 2006/0292174 | A1 | 12/2006 | Rios et al. |
| 2007/0212419 | A1 | 9/2007 | Bako et al. |
| 2007/0243137 | A1 | 10/2007 | Hainfeld |
| 2007/0258889 | A1 | 11/2007 | Douglas et al. |
| 2009/0214663 | A1 | 8/2009 | Albrecht et al. |
| 2009/0274630 | A1 | 11/2009 | Huang |
| 2010/0021503 | A1 | 1/2010 | Denoel et al. |
| 2010/0028994 | A1 | 2/2010 | DeSimone et al. |
| 2011/0256183 | A1* | 10/2011 | Frank .......... A61K 9/5184 424/400 |
| 2011/0280930 | A1 | 11/2011 | Batista et al. |
| 2013/0337066 | A1* | 12/2013 | Zhang .......... A61K 39/0011 424/489 |
| 2016/0136106 | A1 | 5/2016 | Zhang et al. |
| 2017/0000875 | A1 | 1/2017 | Hu |
| 2017/0079909 | A1 | 3/2017 | Zhang et al. |
| 2017/0095510 | A1 | 4/2017 | Lee |
| 2017/0274059 | A1 | 9/2017 | Zhang et al. |
| 2017/0367990 | A1 | 12/2017 | Lee |
| 2018/0085320 | A1 | 3/2018 | Zhang et al. |

FOREIGN PATENT DOCUMENTS

| | | |
|---|---|---|
| CN | 101735613 A | 6/2010 |
| GB | 2482069 A | 1/2010 |
| JP | 2005-525407 A | 8/2005 |
| RU | 2345805 C1 | 2/2009 |
| WO | 2005/020964 A1 | 3/2005 |
| WO | 2008/003524 A2 | 1/2008 |
| WO | 2008/013952 A2 | 1/2008 |
| WO | 2008/150276 A2 | 12/2008 |
| WO | 2010/070620 A2 | 6/2010 |
| WO | 2011/002239 A2 | 1/2011 |
| WO | 2011/116219 A2 | 9/2011 |
| WO | 2013/052167 A2 | 4/2013 |
| WO | 2015/021390 A2 | 2/2015 |
| WO | 2015/187502 A1 | 12/2015 |
| WO | 2016/028965 A1 | 2/2016 |
| WO | 2016/109306 A1 | 7/2016 |
| WO | 2016/153979 A1 | 9/2016 |
| WO | 2016/176041 A1 | 11/2016 |
| WO | 2016/205009 A1 | 12/2016 |
| WO | 2016/205010 A1 | 12/2016 |
| WO | 2017/087897 A1 | 5/2017 |

OTHER PUBLICATIONS

Hu, et al., "Erythrocyte-inspired Delivery Systems," Adv. Healthcare Mater., 2012 1:537-547.

Hung, et al., Small-molecule inhibitor of Vibrio cholerae virulence and intestinal colonization. Science, 2005, 310, 670-674.

Huwyler, et al. By-passing of P-glycoprotein using immunoliposomes. J. Drug Target. 2002 10(1), 73-79.

Jacobs, et al. "An evolution of antimalarial combinations against plasmodium berghei in the mouse," J Parasitol, 1963, 49:920-925.

Jiang, et al., "Ultralow-Fouling, Functionalizable, and Hydrolyzable Zwitterionic Materials and Their Derivatives for Biological Applications." Adv. Mater., 2010, vol. 22, pp. 920-932.

Jianlin, Experimental Study on Magnetized Technique of Doxorubicin-loaded Erythrocytes, Wanfang Data, pp. 13, 21-22, 35, 52, Oct. 19, 2009 (Abstract).

Kirkham, et al., Construction and immunological characterization of a novel nontoxic protective pneumolysin mutant for use in future pneumococcal vaccines. Infect Immun 2006, 74, 586.

Kitchin, N., "Review of diphtheria, tetanus and pertussis vaccines in clinical development," Expert Rev. Vaccines, 2011, 10(5), pp. 605-615.

Klainer, et al., "Staphylococcal Alpha-Hemolysin: Detection on the Erythrocyte Membrane by Immunofluorescence", Science, 1964, vol. 145, No. 3633, pp. 714-715.

Knop, et al., "Poly(ethylene glycol) in Drug Delivery: Pros and Cons as Well as Potential Alternatives." Angew. Chem. Int. Ed., 2010, vol. 49, pp. 6288-6308.

Kum et al., Inhibition of staphylococcal enterotoxin A-induced superantigenic and lethal activities by a monoclonal antibody to toxic shock syndrome toxin-1. J Infect Dis 2001 183, 1739-1748.

Li, et al. The effect of pH on the polymer degradation and drug release from PLGA-mPEG microparticles. J. Appl. Polym. Sci. 2008 109(1), 475-482.

Li, et al "Alpha-Alumina Nanoparticles Induce Efficient Autophagy-Dependent Cross-Presentation and Potent Antitumour Response" Nature Nanotechnology 2011 6, 645-650.

Liu, et al., "Porous nanoparticle supported lipid bilayers (protocells) as delivery vehicles", J Am Chem Soc, 2009, 131:1354-1355.

Lowenberg et al., High-Dose Daunorubicin in Older Patients with Acute Myeloid Leukemia. New Engl. J. Med. 2009 361(13), 1235-1248.

Lund, et al. Efficient isolation and quantitative proteomic analysis of cancer cell plasma membrane proteins for identification of metastasis-associated cell surface markers. J Proteome Res 2009, 8 (6), 3078-3090.

Ma, et al., "Vesicular polydiacetylene sensor for colorimetric signaling of bacterial pore-forming toxin", Langmuir, 2005, 21,6123-6126.

(56) References Cited

OTHER PUBLICATIONS

Markov, et al., "Human Erythrocytes as Nanoparticle Carriers for Magnetic Particle Imaging," Physics in Medicine and Biology, 2010 55(21):6461-6473.

McCormick, et al., Chemical inhibition of alpha-toxin, a key corneal virulence factor of *Staphylococcus aureus*. Invest Ophthalmol Vis Sci 2009 50, 2848-2854.

Merkel, et al. Using mechanobiological mimicry of red blood cells to extend circulation times of hydrogel microparticles. Proc Natl Acad Sci, 2011, vol. 108, No. 2, pp. 586-591.

Metz et al., "Identification of Formaldehyde-induced Modifications in Proteins: Reactions with Model Peptides," J. Bio. Chem., 2004, 279(8), pp. 6235-6243.

Moghimi, et al., "Long-Circulating and Target-Specific Nanoparticles: Theory to Practice." Pharmacal Rev, The American Society for Pharmacology and Experimental Therapeutics, 2001 vol. 53, No. 2, pp. 283-318.

Moon, et al. "Interbilayer-Crosslinked Multilamellar Vesicles as Synthetic Vaccines for Potent Humoral and Cellular Immune Responses." Nature Materials, 2011, 10(3): 243-251.

Moore et al., "Specific Targeting and Delivery of Virus Envelope-Coated Nanoparticle Cargoes into Receptor-Bearing Cells and Subcellular Compartments," NSTI-Nanotech 2007, vol. 2, pp. 370-373.

Moorjani et al., Nanoerythrosomes, a new derivative of erythrocyte ghost II: identification of the mechanism of action. Anticancer Res 2001, 16, 2831-2836.

Mortimer, E.A. Jr., "Immunization against Infectious Disease," Science, 1978, 200, pp. 902-907.

Nakouzi, et al., Passive administration of monoclonal antibodies to anthrolysin O prolong survival in mice lethally Infected with *Bacillus anthracis*. BMC Microbiol 2008, 8(159): 1-10.

Navas, et al., Isolation of purified plasma membranes from cultured cells and hepatomas by two-phase partition and preparative free-flow electrophoresis. Cancer Res 1989, 49 (8), 2147-2156.

O'Hanley, et al. Alpha-hemolysin contributes to the pathogenicity of piliated digalactoside-binding *Escherichia coli* in the kidney: efficacy of an alpha-hemolysin vaccine in preventing renal injury in the BALB/c mouse model of pyelonephritis. Infect Immun, 1991, 59, 1153-1161.

Oldenborg, et al. "Role of CD47 as a marker of self on red blood cells," Science. 2000, 288:2051-2054.

Parish et al., "Staphylococcal Infection: Antitoxic Immunity," Br. Med. J., 1960, 1(5175), pp. 743-747.

Peer, et al., "Nanocarriers as an emerging platform for cancer therapy." Nature anotechnology, 2007, pp. 751-760, vol. 2, pp. 751-760.

Peracchia, et al. "Stealth PEGylaled polycyanoacrylate nanoparticles for intravenous administration and splenic targeting," J Control Release, 1999, 60:121-128.

Petros, et al., Strategies in the design of nanoparticles for therapeutic applications. Nat. Rev. Drug Discov. 9(8), 615-627 (2010).

Petrov et al., "Toxicity and Immunogenicity of Neisseria meningitis Lipopolysaccharide Incorporated into Liposomes," Infect. Immun. 1992, 60(9), pp. 3897-3903.

Pitt et al. The kinetics of drug cleavage and release from matrices containing covalent polymer-drug conjugates. J. Control. Release, 1995, 33(3), 391-395.

Popielarski, et al. "A nanoparticle-based model delivery system to guide the rational design of gene delivery to the liver. 1. Synthesis and characterization," Bioconjug Chem, 2005, 16, pp. 1063-1070.

Pornpattananangkul, et al. Bacterial Toxin-Triggered Drug Release from Gold Nanoparticle-Stabilized Aposomes for the Treatment of Bacterial Infection. J. Am. Chem. Soc. 2011, 133(11), 4132-4139.

Ragle, et al., "Anti-Alpha-Hemolysin Monoclonal Antibodies Mediate Protection against *Staphylococcus aureus* Pneumonia." Infection and Immunity. 2009, 77(7):2712-2718.

Rapoport, et al. Intracellular uptake and trafficking of pluronic micelles in drug-sensitive and MDR cells: Effect on the intracellular drug localization. J. Pharm. Sci. 2002 91(1), 157-170.

Rosado, et al., "The MACPF/CDC family of pore-forming toxins", Cell Microbiol., 2008, 10, 1765-1774.

Tanaka, et al., "Polymer-supported membranes as models of the cell surface," Nature, 2005 437:656-663.

Sahoo et al., "Enhanced Antiproliferative Activity of Transferrin-Conjugated Paclitaxel-Loaded Nanoparticles is Mediated via Sustained Intracellular Drug Retention," Molecular Pharmaceutics, 2005, 2(5):373-383.

Schmitt et al., "Bacterial toxins: friends or foes?," Emerg. Infect. Dis., 1999, 5(2), pp. 224-234.

Sengupta, et al. "Temporal targeting of tumor cells and neovasculature with a nanoscale delivery system," Nature, 2005, 436:568-572.

Shoham, "Antivirulence agents against MRSA", Future Med Chem, 2011, 3, 775-777.

Siepmann, et al. "Higuchi equation: derivation, applications, use and misuse", Int. J. Pharm., 2011, 418(1), 6-12.

Simberg, et al. "Biomimetic amplification of nanoparticle homing to tumors," Proc Nail Acad Sci, 2007, 104:932-936.

Takae, et al, "PEG-detachable polyplex micelles based on disulfide-linked block catiomers as bioresponsive nonviral gene vectors", J. Am. Chem. Soc. 2008, 130(18), 6001-6009.

Tong, et al. Controlled Synthesis of Camptothecin-Polylactide Conjugates and Nanoconjugates. Bioconjug. Chem. 2010 21(1), 111-121.

Tong et al. Ring-opening polymerization-mediated controlled formulation of polylaclide-drug nanoparticles. J. Am. Chem. Soc. 2009 131(13), 4744-4754.

Tsai, et al. "Self inhibition of phagocytosis: the affinity of marker of self CD47 for SIRPalpha dictates potency of Inhibition but only at low expression levels," Blood Cells Mol Dis, 2010, 45:67-74.

Valencia, et al. "Single-step assembly of homogenous lipid-polymeric and lipid-quantum dot nanoparticles enabled by microfluidic rapid mixing," ACS Nano, 2010, 4:1671-1679.

Valeva et al., Membrane Insertion of the Heptameric Staphylococcal a-Toxin Pore. J Bioi Chem 2001, 276, 14835-14844.

Schooneveld, et al. "Imaging and quantifying the morphology of an organic-inorganic nanoparticle at the sub-nanometre level," Nat Nanotechnol, 2010, 5:538-544.

Vandana, et al., The role of the amino terminus in the kinetics and assembly of alpha-hemolysin of *Staphylococcus aureus*. J Bioi Chem, 1997, vol. 272, No. 40, 24858-24863.

Vayro. et al., "Preparation and characterization of basolateral plasma-membrane vesicles from sheep parotid glands: Mechanisms of phosphate and D-glucose transport" Biochem J, 1991, 279, 843-848.

Wardenburg, et al. "Vaccine protection against *Staphylococcus aureus* pneumonia". J Exp Med, 2008, 205, 287.

Watts et al., "Pathways of antigen processing and presentation," Rev. Immunogenet., 1999, 1, pp. 60-74.

Waugh, et al. "Effects of lost surface area on red blood cells and red blood cell survival in mice," Am J Physiol, 1996, 271:C1847-1852.

Wei-Hong et al., "Pharmacokinetics of Morphine Loaded into Erythrocyte in Rabbits," Journal of China Pharmaceutical University, 2006, 37(2):150-152. Abstract.

Xiao, et al. "A self-assembling nanoparticle for paclitaxel delivery in ovarian cancer. Biomaterials," 2009, 30:6006-6016.

Yang, et al., "Functionalizable and ultra stable nanoparticles coated with zwitterionic poly (carboxybetaine) in undiluted blood serum." Biomaterials, 2009, pp. 5617-5621, vol. 30, Elsevier Ltd.

Yoo, et al., "In Vitro and in vivo anti-tumor activities of nanoparticles based on doxorubicin-PLGA conjugates", Journal of Controlled Sciences, 2000, vol. 68, pp. 419-431.

Yoo, et al., "Factors that Control the Circulation Time of Nanoparticles in Blood: Challenges, Solutions and Future Prospects", Current Pharmaceutical Design, 2010, vol. 16, pp. 2298-2307.

Zhang, et al., "Induction of Anti-Tumor Cytotoxic T Cell Responses through PLGA-Nanoparticle Mediated Antigen Delivery." Biomaterials 2011, 32(14):3666-78.

Wang et al, "Size-Dependent Endocytosis of Nanoparticles," Adv. Mater., 2009, 21, pp. 419-424.

Zhang, "Lipid-polymer hybrid nanoparticles: synthesis, characterization and applications," Nano LIFE, 2010, 1:163-173.

(56) References Cited

OTHER PUBLICATIONS

Zhang, et al. "Self-assembled lipid-polymer hybrid nanoparticles: A robust drug delivery platform," ACS Nano, 2008, 2:1696-1702.
Zhang, et al., "Transmembrane Delivery of Aggregated [Gd@C82(OH)22]n Nanoparticles," Journal of Nanoscience and Nanotechnology, 2010 10(12):8556-8561.
Zhao, et al. "Interaction of Mesoporous Silica Nanoparticles with Human Red Blood Cell Membranes: Size and Surface Effects," ACS Nano, 2011, 5(2):1366-1375.
International Preliminary Report on Patentability for PCT/US2014/067688, dated Jun. 7, 2016 (6 pages).
International Search Report and Written Opinion for PCT/US2014/067688, dated Feb. 4, 2015 (198 pages).
Restriction Requirement issued in U.S. Appl. No. 15/100,273, dated Nov. 18, 2016 (9 pages).
Response to Restriction Requirement issued in U.S. Appl. No. 15/100,273, filed Jan. 18, 2017 (10 pages).
Office Action issued in U.S. Appl. No. 15/100,273, dated Feb. 17, 2017 (14 pages).
Taiwanese Office Action for TW Application No. 101119113, dated Jun. 7, 2016 (13 pages with English translation).
Japanese Office Action for JP Application No. 2014-513590, dated Feb. 19, 2016 (9 pages).
Response to Taiwanese Office Action for TW Application No. 101119113, filed on Feb. 5, 2016 (56 pages).
Response to Chinese Office Action for CN Application No. 2012800350485, filed on Jan. 25, 2016 (63 pages).
Taiwanese Office Action for TW Application No. 101119113 dated Oct. 6, 2015 (15 pages).
Office Action issued in Chinese Application No. 201280035048.5, dated Feb. 17, 2015 (17 pages).
Response to Supplementary Search Report for EP Application No. 12838792.5, filed Nov. 24, 2015 (9 pages).
Chinese Office Action for CN Application No. 201280035048.5 dated Nov. 10, 2015 (13 pages).
Extended European Search Report for EP Application No. 12838792.5, dated May 7, 2015 (5 pages).
Supplementary European Search Report for EP Application No. 12838792.5, dated May 27, 2015 (4 pages).
Response to Office Action for Chinese Application No. 201280035048.5, filed on Jul. 6, 2015 and English version of remarks and claims (33 pages).
International Search Report and Written Opinion for PCT/US2012/039411, dated Apr. 8, 2013 (7 pages).
International Preliminary Report on Patentability for PCT Application No. PCT/US2012/039411, dated Apr. 3, 2014 (6 pages).
PCT International Search Report and Written Opinion for PCT Application No. PCT/US2015/021702 (9 pages).
Alexander, et al., "Immunization of mice with pneumolysin toxoid confers a significant degree of protection against at least nine serotypes of *Streptococcus pneumoniae*", Infect Immun 1994, 62, 5683-5688.
Alexis, et al., "Factors Affecting the Clearance and Biodistribution of Polymeric Nanoparticles", Molecular Pharmaceutics, 2008, vol. 5, No. 4, pp. 505-515.
Andreeva-Kovolevskaya, et al., Pore-forming proteins and adaptation of living organisms to environmental conditions. Biochemistry (Moscow) 2008, 73, 1473-1492.
Antonelli, et al., "New Biomimetic Constructs for Improved In Vivo Circulation of Superparamagnetic Nanoparticles," Nanoscience and Nanotechnology, 2008, 8(5)2270-2278.
Antonelli, et al., "Encapsulation of Superparamagnetic Nanoparticles into Red Blood Cells as New Carriers of MRI Contrast Agents", Nanomedicine, 2011 6(2):211-223.
Arnold, et al. "NanoCipro encapsulation in monodisperse large porous PLGA microparticles", J Control Release, 2007, 121:100-109.

Aryal. et al. "Polymeric Nanoparticles with Precise Ratiometric Control over Drug Loading for Combination Therapy", Mol. Pharmaceutics. 2011, vol. 8, pp. 1401-1407, American Chemical Society.
Aryal, et al. "Polymer-Cisplatin Conjugate Nanoparticles for Acid-Responsive Drug Delievery", 2010, vol. 4, No. 1, pp. 251-258.
Avgoustakis, et al. "Effect of copolymer composition on the physicochemical characteristics, in vitro stability, and biodistribution of PLGA-mPEG nanoparticles" J Pharm 2003, 259:115-127.
Avgoustakis, et al. "PLGA-mPEG nanoparticles of cisplatin: in vitro nanoparticle degradation, in vitro drug release and in Vivo drug residence in blood properties," J. Control. Release 2002, 79(1-3), 123-135.
Beghini, et al., "Anti-sera raised in rabbits against crotoxin and phospholipase A2 from Crotalus durissus cascavella ienom neutralize the neurotoxicity of the venom and crotoxin", Toxicon 2004, 44, 141-148.
Blum, et al., "Pathways of Antigen Processing," Annu. Rev. Immunol. 2013, 31, pp. 443-473.
Boes, et al., "Endosomal processing for antigen presentation mediated by CD1 and Class I major histocompatibility Complex: roads to display or destruction," Immunology, 2009, 127(2), pp. 163-170.
Boone, et al., Isolation of plasma membrane fragments from HeLa cells. J Cell Biol 1969, 41 (2), 378-392.
Brahler, et al., "Magnetite-Loaded Carrier Erythrocytes as Contrast Agents for Magnetic Resonance Imaging," American Chemical Society, Nano Letters 2006 6(11):2505-2509.
Branton, et al, "The potential and challenges of nanopore sequencing", Nat Biotechnol, 2008 26, 10, 1146-1153.
Budhian, et al. Controlling the in vitro release profiles for a system of haloperidol-loaded PLGA nanoparticles. Int. J. Pharm. 2008 346(1-2), 151-159.
Chalmeau et al. "Alpha-Hemolysin pore formation into a supported phospholipid bilayer using cell-free expression", Biochim Biophys Acta, 2011, 1808, 271-278.
Chen et al., Potent neutralization of anthrax edema toxin by a humanized monoclonal antibody that competes with calmodulin for edema factor binding. Proc Nail Acad Sci 2009 106, 13487-13492.
Cheng, et al. "Formulation of functionalized PLGA-PEG nanoparticles for in vivo targeted drug delivery", Biomaterials, 2007, 28:869-876.
Cho, et al. "A Multifunctional Core-Shell Nanoparticle for Dendritic Cell-Based Cancer Immunotherapy", Nature Nanotechnology 2011 6, 675-82.
Clatworthy, et al., "Targeting virulence: a new paradigm for antimicrobial therapy", Nat Chem Biol, 2007, 3, 541-548.
Cryz, Jr. et al., "Effect of Chemical and Heat Inactivation on the Antigenicity and Immunogenicity of Vibrio Cholerae," Infect. Immun., 1982, 38(1), pp. 21-26.
Davis, et al., "Nanoparticle therapeutics: an emerging treatment modality for cancer." Nature Reviews/Drug Discovery, 2008, pp. 71-782, vol. 7, pp. 771-782.
Desilets, et al. "Nanoerythrosomes, a new derivative of erythrocyte ghost: IV. Fate of reinjected nanoerythrosomes," Anticancer Res, 2001, vol. 21, pp. 1741-1747.
Dodge, et al. "The preparation and chemical characteristics of hemoglobin-free ghosts of human erythrocytes," Arch Biochem Biophys, 1963, 100:119-130.
Doshi, et al., "Red Blood Cell-Mimicking Synthetic Biomaterial Particles," PNAS, 2009 106(51):21495-21499.
Eaton, "Chemical Modification of Purified Diphtheria Toxin." The Journal of Immunology. 1937 (33): 419-436.
Edelson, et al. Intracellular antibody neutralizes Listeria growth. Immunity 2001, 14, 503-512.
Edelson, et al., Cutting edge: paradigm revisited: antibody provides resistance to Listeria infection. J Immunol 1999, 163, 4087-4090.
Fang, et al. "Quick synthesis of lipid-polymer hybrid nanoparticles with low polydispersity using a single-step sonication method," Langmuir, 2010 26:16958-16962.
Farokhzad, et al., Impact of Nanotechnology on Drug Delivery. ACS Nano 2009, 3(1), 16-20.
Gao, et al. "pH-Responsive Nanoparticles for Drug Delivery", Mol. Pharm. 2010, 7(6), 1913-1920.

(56) References Cited

OTHER PUBLICATIONS

Geng, et al., "Shape effects of filaments versus spherical particles in flow and drug delivery." Nature Nanotechnology, 2007, pp. 249-255, vol. 2, pp. 249-255.

Gilbert, "Pore-forming toxins," Cell Mol Life Sci, 2002, 59, 832-844.

Goshi, et al., "Studies on the Pathogenesis of Staphylococcal Infection." The Journal of Experimental Medicine. 1961, 113(2): 259-270.

Goutayer, et al. "Tumor targeting offunctionalized lipid nanoparticles: assessment by in vivo fluorescence imaging," Eur J Pharm Biopharm, 2010, 75, 137-147.

Graham, "Isolation of membranes from tissue culture cells", Methods Mol Biol, 1993, 19, 97-108.

Gratton, et al. "Nanofabricated particles for engineered drug therapies: a preliminary biodistribution study of PRINT nanoparticles," J Control Release, 2007, 121:10-18.

Greenberg et al., "Phase I dose finding studies of an adjuvanted Clostridium difficile toxoid vaccine," Vaccine, 2012, 30, pp. 2245-2249.

Gu, et al. "Precise engineering of targeted nanoparticles by using self-assembled biointegrated block copolymers" Proc Nail Acad Sci USA, 2008, 105:2586-2591.

Hamidi, et al., "Encapsulation of Valproate-Loaded Hydrogel Nanoparticles in Intact Human Erythrocytes: A Novel Nano-Cell Composite for Drug Delivery," Journal of Pharmaceutical Sciences, 2011 100(5):1702-1711.

Harush-Frenkel, et al., "Targeting of nanoparticles to the clathrin-mediated endocytic pathway," Biochem. Biophys. Res. Commun., 2007, 353, pp. 26-32.

Henon, et al., Isolation, identification and characterization of a plasma membrane preparation of guinea pig macrophages C R Acad Sci Hebd Seances Acad Sci D 1977, 285 (1), 121-122.

Higuchi. Rate of release of medicaments from ointment bases containing drugs in suspension. J. Pharm. Sci. 1961 50, 874-875.

Hochmuth, et al., "Mechanical measurement of red cell membrane thickness" Science, 1983 220:101-102.

Holmgren et al., "Development of improved cholera vaccine based on subunit toxoid," Nature, 1977, 269, pp. 602-604.

Hoshino et al., "Recognition, neutralization, and clearance of target peptides in the bloodstream of living mice by molecularly imprinted polymer nanoparticles: a plastic antibody", J Am Chem Soc, 2010, 132, 6644-6645.

Hoshino et al., "The rational design of a synthetic polymer nanoparticle that neutralizes a toxic peptide in vivo", Proc Nail Acad Sci, 2012, 109, 33.

Hu, et al. Therapeutic Nanoparticles to Combat Cancer Drug Resistance. Curr. Drug Metab. 2009 10(8), 836-841.

\* cited by examiner

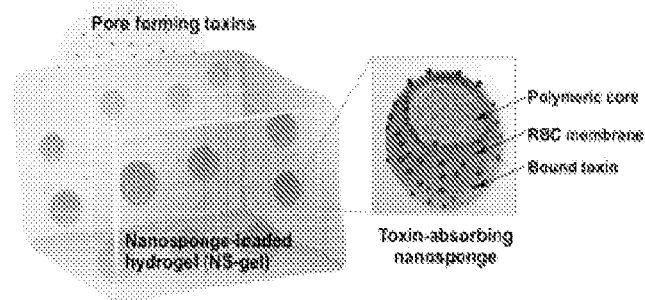
FIGURE 7A
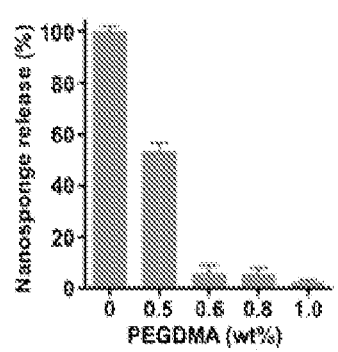 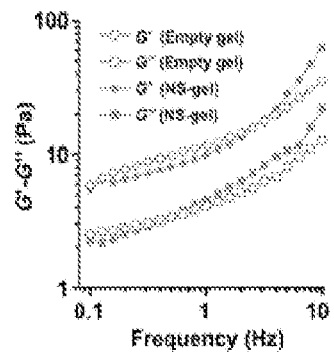
FIGURE 7B                FIGURE 7C
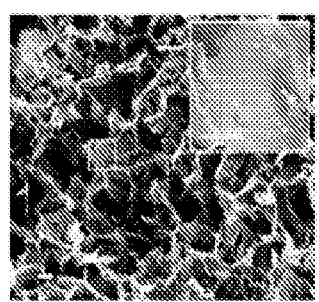 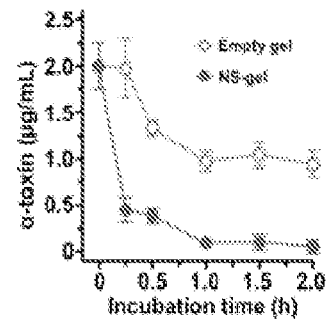
FIGURE 7D                FIGURE 7E

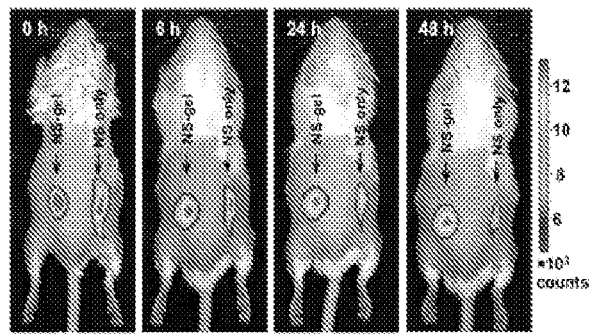 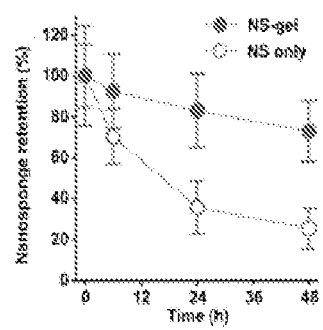
FIGURE 9A                    FIGURE 9B
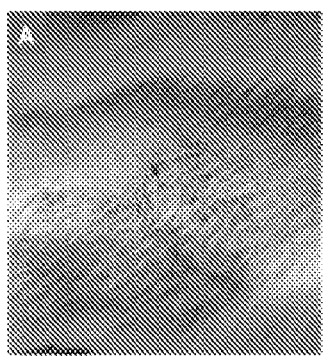 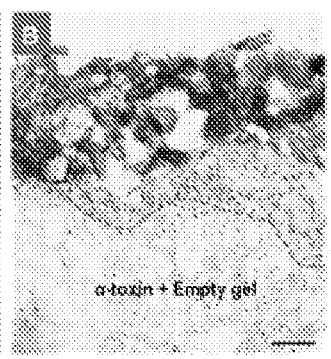 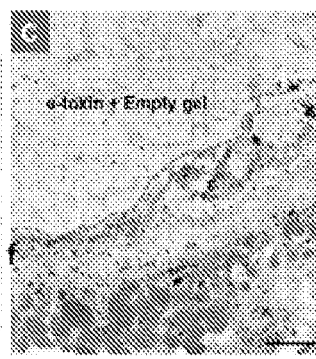
FIGURE 10A          FIGURE 10B          FIGURE 10C
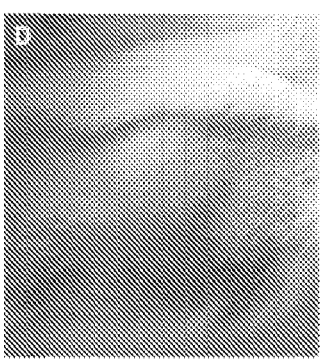 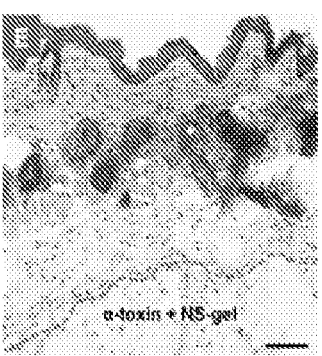 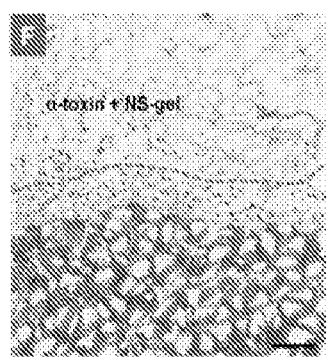
FIGURE 10D          FIGURE 10E          FIGURE 10F

HYDROGEL TOXIN-ABSORBING OR BINDING NANOPARTICLES

CROSS REFERENCE TO RELATED APPLICATIONS

This application is a divisional of U.S. application Ser. No. 15/126,342, filed Sep. 15, 2016, which claims the priority benefit of PCT/US2015/021702 filed on Mar. 20, 2015 which claims priority benefit to U.S. Provisional Patent Application No. 61/955,962, filed Mar. 20, 2014, entitled "Biomimetic Toxin Nanosponges," the entire contents of which is incorporated by reference herewith.

STATEMENT REGARDING FEDERALLY SPONSORED RESEARCH

This invention was made with Government support awarded by the National Institute of Diabetes and Digestive and Kidney Diseases of the National Institutes of Health under Grant Number R01DK095168. The United States Government has certain rights in this invention pursuant to this grant.

FIELD OF THE INVENTION

The present invention relates to compositions comprising a polymeric hydrogel impregnated with a toxin-absorbing or binding nanoparticle. The present invention also relates to the use of the above compositions for decreasing or neutralizing the effect of a toxin, or for treating or preventing an infection by a microbe that produces a toxin, in a subject. Exemplary toxins include biological toxins such as a viral, bacterial, fungal, plant or animal toxin.

BACKGROUND OF THE INVENTION

Antimicrobial hydrogels have many applications in combating localized microbial threats. Various antimicrobial hydrogel formulations have been applied to facilitate bacterial eradication, promote wound healing, and to prevent implant fouling (1a, 2a). These formulations typically consist of highly hydrated biomaterials prepared from natural or synthetic polymers and loaded with common antibiotic drugs (3a, 4a). Despite extensive development on antimicrobial hydrogels, no formulation has been demonstrated to incorporate the capability to eliminate virulence factors produced from infectious microbes. These virulence factors can promote local inflammations and worsen the clinical outcome of the infections (5a).

Membrane coated nanoparticles have been demonstrated to detoxify many membrane-damaging bacterial virulence factors (8a, 9a). However, their applications have so far been limited to systemic administrations, as the particle-stabilized lipid membrane structure, an essential feature for toxin absorption, needs to be in a hydrated state for proper functions. Applying the nanoparticles for topical treatment or for device coating are thus challenging as the formulations can dehydrate quickly.

SUMMARY OF THE INVENTION

In one aspect, the present invention provides for a composition comprising a polymeric hydrogel impregnated with a toxin-absorbing or binding nanoparticle, wherein said nanoparticle comprises a) an inner core comprising a non-cellular material, and b) an outer surface comprising a cellular membrane configured for absorbing or binding said toxin.

In another aspect, the present invention provides for a method for decreasing or neutralizing the effect of a toxin, or for treating or preventing an infection by a microbe that produces a toxin, in a subject, which method comprises administering, to a subject in need, or to cells of said subject, an effective amount of the above composition.

In still another aspect, the present invention provides for a method of preserving therapeutic functionality of a toxin-absorbing or binding nanoparticle, which method comprises impregnating a toxin-absorbing or binding nanoparticle in a polymeric hydrogel to form a composition comprising said polymeric hydrogel impregnated with said toxin-absorbing or binding nanoparticle, wherein said nanoparticle comprises a) an inner core comprising a non-cellular material, and b) an outer surface comprising a cellular membrane configured for absorbing or binding said toxin.

In yet another aspect, the present invention provides for use of an effective amount of a composition comprising a polymeric hydrogel impregnated with a toxin-absorbing or binding nanoparticle for the manufacture of a medicament for decreasing or neutralizing the effect of a toxin, or for treating or preventing an infection by a microbe that produces a toxin, in a subject, wherein said nanoparticle comprises a) an inner core comprising a non-cellular material, and b) an outer surface comprising a cellular membrane configured for absorbing or binding said toxin.

As infectious bacteria rely on many virulence factors for survival and colonization (6a, 7a), a toxin-neutralizing antimicrobial hydrogel formulation can be useful in enhancing bactericidal effect via the synergism between antibiotics and anti-virulence treatments. In some embodiments, the present invention incorporates a broadly applicable toxin-neutralizing nanoparticle platform with antimicrobial hydrogels for infection treatment and prophylaxis. In some embodiments, incorporating toxin-neutralizing membrane coated nanoparticles with hydrogels enables the particles to retain their functionality, as hydrogels retain water molecules within its structures (up to 99.6 wt % of water). By combining hydrogel formulations with membrane coated nanoparticles, a toxin detoxifying hydrogel formulation can thus be prepared. Given the cargo loading capacity of hydrogels and polymeric particles, antibiotics can be encapsulated to the toxin-neutralizing hydrogels.

In some aspects, the prevent disclosure relates to U.S. application Ser. No. 13/827,906, filed Mar. 14, 2013, International Application No. PCT/US2012/039411, filed May 24, 2012 and published as WO 2013/052167 A2 and U.S. provisional application Ser. No. 61/492,626, filed Jun. 2, 2011. The contents of the above applications are incorporated by reference in their entireties.

BRIEF DESCRIPTION OF THE DRAWINGS

FIGS. 6A and 6B showed the images of mice skin of nanosponge hydrogel group and hydrogel group, respectively. Images of H.E. stained sections of mice skin from the above nanosponge hydrogel are shown in group 6C or hydrogel group 6D. Images of TUNEL stained sections of mice skin from the above nanosponge hydrogel are shown in group 6E or hydrogel group 6F.

FIGS. 7A-7E illustrates formulation and characterization of nanosponge-loaded hydrogel (NS-gel). FIG. 7A Schematic illustration of a hydrogel retaining toxin-absorbing nanosponges for local treatment of methicillin-resistant *Staphylococcus aureus* (MRSA) infection. The toxin nanosponge was constructed with a polymeric core wrapped in natural red blood cell (RBC) bilayer membrane and was subsequently embedded into an acrylamide-based hydrogel. FIG. 7B Release of the toxin nanosponge from hydrogels made with different crosslinker concentrations. Error bars represent the standard deviations (n=3). FIG. 7C Rheological characterization of the hydrogel (0.6 wt % crosslinker) either without nanosponges (open markers) or loaded with 2 mg/mL nanosponges (solid markers). The storage modulus G' and loss modulus G" were plotted logarithmically against frequency (0.1-10 Hz at 37° C.). FIG. 7D A representative scanning electron microscope (SEM) image of the NS-gel. The scale bar represents 1 μm. FIG. 7E Absorption of α-toxin was studied by incubating 1 mL α-toxin solution (2 μg/mL in PBS) with 1 mL NS-gel or empty gel. The concentrations of α-toxin in the supernatant at different incubation times were quantified using ELISA. Error bars represent standard deviations (n=3).

FIG. 8A Centrifuged RBCs after incubation with α-toxin mixed in PBS, empty gel, and NS-gel, respectively. FIG. 8B Hemolysis quantification of the samples in FIG. 8A. FIG. 8C Centrifuged RBCs after incubation with MRSA-culturing medium mixed with PBS, empty gel, and NS-gel, respectively. FIG. 8D Hemolysis quantification of the samples in FIG. 8C. Error bars represent standard deviations (n=3).

FIGS. 9A-9B illustrates in vivo nanosponge retention by hydrogel. Nanosponges labeled with DiD fluorescent dye was used to formulate NS-gel, which was then injected subcutaneously under the loose skin over the left flank of the mice. Free suspended nanosponeges (without hydrogel) were injected as a control group at the right flank of the same mice. FIG. 9A Fluorescence images taken at different time points show the retention of the nanosponges under mouse skin. FIG. 9B Quantification of the fluorescence intensity as observed in FIG. 9A. All images are representative of 3 mice per group and the error bars represent the standard deviation (n=3).

FIGS. 10A-10F illustrates in vivo toxin neutralization. FIGS. 10A-10C, Mice injected with α-toxin followed by empty gel. The dashed lines depict the approximate tissue-hydrogel boundary. FIG. 10A Skin lesions occurred 72 h following toxin injection. FIG. 10B Hematoxylin and eosin (H&E) stained histological sections revealed inflammatory infiltrate, apoptosis, necrosis and oedema in the epidermis. FIG. 10C Tears on muscle fibres, interfibril oedema and extravasation of neutrophils from surrounding vasculature indicate muscular damage. FIGS. 10D-10F, Mice injected with α-toxin followed by NS-gel. FIG. 10D No skin lesion occurred. FIG. 10E No abnormality was observed in the epidermis. FIG. 10F Normal muscle structure was observed. Scale bar represents 50 μm, n=6 for each group.

DETAILED DESCRIPTION OF THE INVENTION

Figure 1:
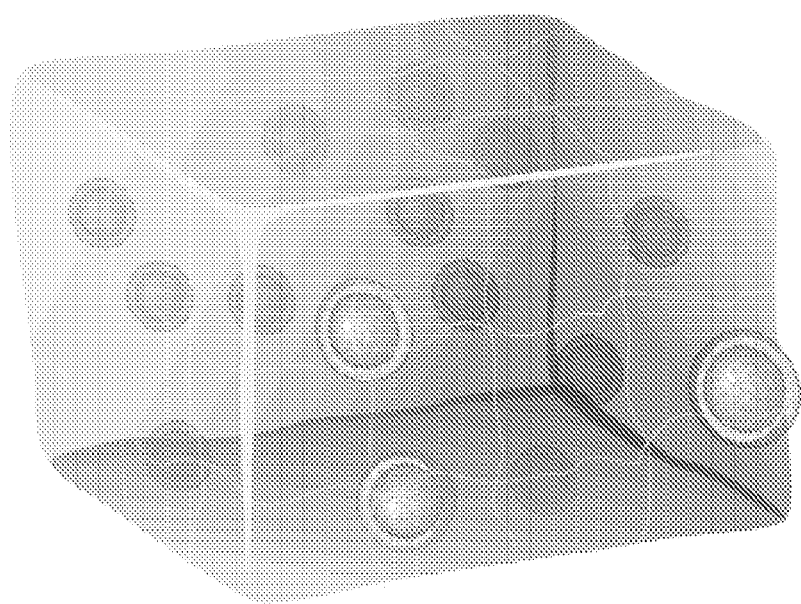
FIG. 1 illustrates a schematic representation of a toxin-neutralizing hydrogel, which comprises or consists of a hydrogel matrix doped with toxin-neutralizing nanoparticles.

The practice of the present invention will employ, unless otherwise indicated, conventional techniques of nanotechnology, nano-engineering, molecular biology (including recombinant techniques), microbiology, cell biology, biochemistry, immunology, and pharmacology, which are within the skill of the art. Such techniques are explained fully in the literature, such as, *Molecular Cloning: A Laboratory Manual*, $2^{nd}$ ed. (Sambrook et al., 1989); *Oligonucleotide Synthesis* (M. J. Gait, ed., 1984); *Animal Cell Culture* (R. I. Freshney, ed., 1987); *Methods in Enzymology* (Academic Press, Inc.); *Current Protocols in Molecular Biology* (F. M. Ausubel et al., eds., 1987, and periodic updates); *PCR: The Polymerase Chain Reaction* (Mullis et al., eds., 1994); and Remington, *The Science and Practice of Pharmacy*, $22^{th}$ ed., (Pharmaceutical Press and Philadelphia College of Pharmacy at University of the Sciences 2012).

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference.

A. Definitions

To facilitate understanding of the invention, a number of terms and abbreviations as used herein are defined below as follows:

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

Cellular Membrane: The term "cellular membrane" as used herein refers to a biological membrane enclosing or separating structure acting as a selective barrier, within or around a cell or an emergent viral particle. The cellular membrane is selectively permeable to ions and organic molecules and controls the movement of substances in and out of cells. The cellular membrane comprises a phospholipid uni- or bilayer, and optionally associated proteins and carbohydrates. As used herein, the cellular membrane refers to a membrane obtained from a naturally occurring biological membrane of a cell or cellular organelles, or one derived therefrom. As used herein, the term "naturally occurring" refers to one existing in nature. As used herein, the term "derived therefrom" refers to any subsequent modification of the natural membrane, such as isolating the cellular membrane, creating portions or fragments of the membrane, removing and/or adding certain components, such as lipid, protein or carbohydrates, from or into the membrane taken from a cell or a cellular organelle. A membrane can be derived from a naturally occurring membrane by any suitable methods. For example, a membrane can be prepared or isolated from a cell or a virus and the prepared or isolated membrane can be combined with other substances or materials to form a derived membrane. In another example, a cell or virus can be recombinantly engineered to produce "non-natural" substances that are incorporated into its membrane in vivo, and the cellular or viral membrane can be prepared or isolated from the cell or the virus to form a derived membrane.

In various embodiments, the cellular membrane covering either of the unilamellar or multilamellar nanoparticles can be further modified to be saturated or unsaturated with other lipid components, such as cholesterol, free fatty acids, and phospholipids, also can include endogenous or added proteins and carbohydrates, such as cellular surface antigen. In such cases, an excess amount of the other lipid components can be added to the membrane wall which will shed until the concentration in the membrane wall reaches equilibrium, which can be dependent upon the nanoparticle environment. Membranes may also comprise other agents that may or may not increase an activity of the nanoparticle. In other examples, functional groups such as antibodies and aptamers can be added to the outer surface of the membrane to enhance site targeting, such as to cell surface epitopes found in cancer cells. The membrane of the nanoparticles can also comprise particles that can be biodegradable, cationic nanoparticles including, but not limited to, gold, silver, and synthetic nanoparticles.

Synthetic or artificial membrane: As used herein, the term "synthetic membrane" or "artificial membrane" refers to a man-made membrane that is produced from organic material, such as polymers and liquids, as well as inorganic materials. A wide variety of synthetic membranes are well known in the art.

Nanoparticle: The term "nanoparticle" as used herein refers to nanostructure, particles, vesicles, or fragments thereof having at least one dimension (e.g., height, length, width, or diameter) of between about 1 nm and about 10 µm. For systemic use, an average diameter of about 50 nm to about 500 nm, or 100 nm to 250 nm may be preferred. The term "nanostructure" includes, but is not necessarily limited to, particles and engineered features. The particles and engineered features can have, for example, a regular or irregular shape. Such particles are also referred to as nanoparticles. The nanoparticles can be composed of organic materials or other materials, and can alternatively be implemented with porous particles. The layer of nanoparticles can be implemented with nanoparticles in a monolayer or with a layer having agglomerations of nanoparticles. In some embodiments, the nanoparticle comprising or consisting an inner core covered by an outer surface comprising the membrane as discussed herein. The invention contemplates any nanoparticles now known and later developed that can be coated with the membrane described herein.

Pharmaceutically active: The term "pharmaceutically active" as used herein refers to the beneficial biological activity of a substance on living matter and, in particular, on cells and tissues of the human body. A "pharmaceutically active agent" or "drug" is a substance that is pharmaceutically active and a "pharmaceutically active ingredient" (API) is the pharmaceutically active substance in a drug.

Pharmaceutically acceptable: The term "pharmaceutically acceptable" as used herein means approved by a regulatory agency of the Federal or a state government or listed in the U.S. Pharmacopoeia, other generally recognized pharmacopoeia in addition to other formulations that are safe for use in animals, and more particularly in humans and/or non-human mammals.

Pharmaceutically acceptable salt: The term "pharmaceutically acceptable salt" as used herein refers to acid addition salts or base addition salts of the compounds, such as the multi-drug conjugates, in the present disclosure. A pharmaceutically acceptable salt is any salt which retains the activity of the parent nanoparticle or compound and does not impart any deleterious or undesirable effect on a subject to whom it is administered and in the context in which it is administered. Pharmaceutically acceptable salts may be derived from amino acids including, but not limited to, cysteine. Methods for producing compounds as salts are known to those of skill in the art (see, for example, Stahl et al., Handbook of Pharmaceutical Salts: Properties, Selection, and Use, Wiley-VCH; Verlag Helvetica Chimica Acta, Zurich, 2002; Berge et al., J Pharm. Sci. 66: 1, 1977). In some embodiments, a "pharmaceutically acceptable salt" is intended to mean a salt of a free acid or base of a nanoparticle or compound represented herein that is non-toxic, biologically tolerable, or otherwise biologically suitable for administration to the subject. See, generally, Berge, et al., J. Pharm. Sci., 1977, 66, 1-19. Preferred pharmaceutically acceptable salts are those that are pharmacologically effective and suitable for contact with the tissues of subjects without undue toxicity, irritation, or allergic response. A nanoparticle or compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

Examples of pharmaceutically acceptable salts include sulfates, pyrosul fates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, [gamma]-hydroxybutyrates, glycolates, tartrates, and mandelates.

Pharmaceutically acceptable carrier: The term "pharmaceutically acceptable carrier" as used herein refers to an excipient, diluent, preservative, solubilizer, emulsifier, adjuvant, and/or vehicle with which a nanoparticle or compound, such as a multi-drug conjugate, is administered. Such carriers may be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art. See, e.g., Remington, The Science and Practice of Pharmacy. 20'" ed., (Lippincott, Williams & Wilkins 2003). Except insofar as any conventional media or agent is incompatible with the active compound, such use in the compositions is contemplated.

Phospholipid: The term "phospholipid", as used herein, refers to any of numerous lipids contain a diglyceride, a phosphate group, and a simple organic molecule such as choline. Examples of phospholipids include, but are not limited to, Phosphatide acid (phosphatidate) (PA), Phosphatidylethanolamine (cephalin) (PE), Phosphatidylcholine (lecithin) (PC), Phosphatidylserine (PS), and Phosphoinositides which include, but are not limited to, Phosphatidylinositol (PI), Phosphatidylinositol phosphate (PIP), Phosphatidylinositol bisphosphate (PIP2) and Phosphatidylinositol triphosphate (PIP3). Additional examples of PC include DDPC, DLPC, DMPC, DPPC, DSPC, DOPC, POPC, DRPC, and DEPC as defined in the art.

Therapeutically Effective Amount: As used herein, the term "therapeutically effective amount" refers to those amounts that, when administered to a particular subject in view of the nature and severity of that subject's disease or condition, will have a desired therapeutic effect, e.g., an amount which will cure, prevent, inhibit, or at least partially arrest or partially prevent a target disease or condition. More specific embodiments are included in the Pharmaceutical Preparations and Methods of Administration section below. In some embodiments, the term "therapeutically effective amount" or "effective amount" refers to an amount of a therapeutic agent that when administered alone or in combination with an additional therapeutic agent to a cell, tissue, or subject is effective to prevent or ameliorate the disease or condition such as a hemolytic disease or condition, or the progression of the disease or condition. A therapeutically effective dose further refers to that amount of the therapeutic agent sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously.

"Treating" or "treatment" or "alleviation" refers to therapeutic treatment wherein the object is to slow down (lessen) if not cure the targeted pathologic condition or disorder or prevent recurrence of the condition. A subject is successfully "treated" if, after receiving a therapeutic amount of a therapeutic agent, the subject shows observable and/or measurable reduction in or absence of one or more signs and symptoms of the particular disease. Reduction of the signs or symptoms of a disease may also be felt by the patient. A patient is also considered treated if the patient experiences stable disease. In some embodiments, treatment with a therapeutic agent is effective to result in the patients being disease-free 3 months after treatment, preferably 6 months, more preferably one year, even more preferably 2 or more years post treatment. These parameters for assessing successful treatment and improvement in the disease are readily measurable by routine procedures familiar to a physician of appropriate skill in the art.

As used herein, "preventative" treatment is meant to indicate a postponement of development of a disease, a symptom of a disease, or medical condition, suppressing symptoms that may appear, or reducing the risk of developing or recurrence of a disease or symptom. "Curative" treatment includes reducing the severity of or suppressing the worsening of an existing disease, symptom, or condition.

The term "combination" refers to either a fixed combination in one dosage unit form, or a kit of parts for the combined administration where a nanoparticle or compound and a combination partner (e.g., another drug as explained below, also referred to as "therapeutic agent" or "co-agent") may be administered independently at the same time or separately within time intervals, especially where these time intervals allow that the combination partners show a cooperative, e.g., synergistic effect. The terms "co-administration" or "combined administration" or the like as utilized herein are meant to encompass administration of the selected combination partner to a single subject in need thereof (e.g., a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g., a nanoparticle or compound and a combination partner, are both administered to a patient simultaneously in the form of a single entity or dosage. The term "non-fixed combination" means that the active ingredients, e.g., a nanoparticle or compound and a combination partner, are both administered to a patient as separate entities either simultaneously, concurrently or sequentially with no specific time limits, wherein such administration provides therapeutically effective levels of the two moieties or compounds in the body of the patient. The latter also applies to cocktail therapy, e.g., the administration of three or more active ingredients.

It is understood that aspects and embodiments of the invention described herein include "consisting" and/or "consisting essentially of" aspects and embodiments.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein, a subject in need refers to an animal, a non-human mammal or a human. As used herein, "animals" include a pet, a farm animal, an economic animal, a sport animal and an experimental animal, such as a cat, a dog, a horse, a cow, an ox, a pig, a donkey, a sheep, a lamb, a goat, a mouse, a rabbit, a chicken, a duck, a goose, a primate, including a monkey and a chimpanzee.

Other objects, advantages and features of the present invention will become apparent from the following specification taken in conjunction with the accompanying drawings.

B. Compositions Comprising a Polymeric Hydrogel Impregnated with a Toxin-Absorbing or Binding Nanoparticle In one aspect, the present invention provides for a composition comprising a polymeric hydrogel impregnated with a toxin-absorbing or binding nanoparticle, wherein said nanoparticle comprises a) an inner core comprising a noncellular material, and b) an outer surface comprising a cellular membrane configured for absorbing or binding said toxin.

Any suitable polymeric hydrogel can be used in the present composition. In some embodiments, the polymeric hydrogel can comprise a material selected from the group consisting of poly(ethylene glycol) dimethacrylate (PEGDMA), silicone, gelatin, chitosan, alginate, polyester, poly(vinyl alcohol) and polyacrylamide, polyethylene oxide, polyvinyl alcohol, CARBOPOL, polyacrylamidomethylpropanesulfonate, polyacrylic acid, a salt of acrylic acid (including sodium and sulfopropyl acrylate, 2-hydroxyethyl methacrylate), agarose, methylcellulose, hyaluronan, and copolymers thereof. In a specific example, the polymeric hydrogel can comprise poly(ethylene glycol) dimethacrylate (PEGDMA).

During manufacture, transportation and/or storage, the polymeric hydrogel in the present composition can be in any suitable form. For example, during manufacture, transportation and/or storage, the polymeric hydrogel in the present composition can be in hydrated or dehydrated form. In some embodiments, during manufacture, transportation and/or storage, the polymeric hydrogel in the present composition can be in hydrated, e.g., comprising at least about 1% (w/w), 2% (w/w), 3% (w/w), 4% (w/w), 5% (w/w), 6% (w/w), 7% (w/w), 8% (w/w), 9% (w/w), 10% (w/w), 20% (w/w), 30% (w/w), 40% (w/w), 50% (w/w), 60% (w/w), 70% (w/w), 80% (w/w), 90% (w/w), 91% (w/w), 92% (w/w), 93% (w/w), 94% (w/w), 95% (w/w), 96% (w/w), 97% (w/w), 98% (w/w), 99% (w/w), or more of water content. In other embodiments, during manufacture, transportation and/or storage, the polymeric hydrogel in the present composition can be in dehydrated form, e.g., in a dry or powder form. During use, the polymeric hydrogel in the present composition can be in hydrated form. For example, during use, the polymeric hydrogel in the present composition can comprise at least about 1% (w/w), 2% (w/w), 3% (w/w), 4% (w/w), 5% (w/w), 6% (w/w), 7% (w/w), 8% (w/w), 9% (w/w), 10% (w/w), 20% (w/w), 30% (w/w), 40% (w/w), 50% (w/w), 60% (w/w), 70% (w/w), 80% (w/w), 90% (w/w), 91% (w/w), 92% (w/w), 93% (w/w), 94% (w/w), 95% (w/w), 96% (w/w), 97% (w/w), 98% (w/w), 99% (w/w), or more of water content.

The polymeric hydrogel in the present composition can possess any suitable degree of flexibility. In some embodiments, the polymeric hydrogel can possess a degree of flexibility suitable to be applied to a tissue or an organ. In other embodiments, the polymeric hydrogel can possess a degree of flexibility suitable to be applied to a natural tissue or a natural organ.

The nanoparticle in the present composition can comprise any suitable inner core. For example, the inner core of the nanoparticle can comprise a polymeric particle core, a silica particle core, or a metal, e.g., gold, particle core. Any suitable polymeric particle core can be used. In some embodiments, the polymeric particle core can comprise an optical shift property. In other embodiments, the polymeric particle core can comprise a metal, e.g., gold, iron oxide or a quantum dot. In still other embodiments, the inner core of the nanoparticle can comprise a biocompatible or a synthetic material, such as poly(lactic-c-glycolic acid) (PLGA), polylactic acid (PLA), polyglycolic acid (PGA), polycaprolactone (PCL), polylysine, and polyglutamic acid. In yet other embodiments, the inner core of the nanoparticle supports the outer surface.

The nanoparticle can comprise a cellular membrane derived from any suitable cell that is a target or that absorbs or binds to a toxin. For example, the nanoparticle can comprise a plasma membrane or an intracellular membrane derived from a cell that is a target or that absorbs or binds to a toxin. The nanoparticle can comprise any suitable cellular membrane derived from a red blood cell. For example, the nanoparticle can comprise a plasma membrane or an intracellular membrane derived from a red blood cell. In some embodiments, the cellular membrane comprises a plasma membrane derived from a red blood cell, a lymphocyte or a platelet, e.g., a plasma membrane derived from a human red blood cell, lymphocyte or platelet. In some embodiments, the nanoparticle can comprise any suitable naturally occurring cellular membrane derived from a red blood cell, a lymphocyte or a platelet. In some embodiments, the cellular membrane comprises a naturally occurring plasma membrane derived from a red blood cell, a lymphocyte or a platelet, e.g., a naturally occurring plasma membrane derived from a human red blood cell, lymphocyte or platelet. In some embodiments, the cellular membrane of the nanoparticle comprises membrane-bound proteins or glycans.

The nanoparticle in the present composition can have any suitable size. For example, the nanoparticle can have a diameter from about 10 nm to about 10 μm. In certain embodiments, the diameter of the nanoparticle is about 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 200 nm, 300 nm, 400 nm, 500 nm, 600 nm, 700 nm, 800 nm, 900 nm, 1 μm, 2 μm, 3 μm, 4 μm, 5 μm, 6 μm, 7 μm, 8 μm, 9 μm, and 10 μm.

The nanoparticle in the present composition can have any suitable shape, including but not limited to, sphere, square, rectangle, triangle, circular disc, cube-like shape, cube, rectangular parallelepiped (cuboid), cone, cylinder, prism, pyramid, right-angled circular cylinder and other regular or irregular shape.

In some embodiments, the nanoparticle in the present composition substantially lacks constituents of the cell, e.g., red blood cell, from which the cellular membrane is derived. For example, the nanoparticle can lack at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the constituents of the cell, e.g., the red blood cell, from which the cellular membrane is derived. In some embodiments, the nanoparticle comprises a plasma membrane derived from a red blood cell and the nanoparticle substantially lacks hemoglobin. For example, the nanoparticle can lack at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the hemoglobin.

In some embodiments, the nanoparticle in the present composition substantially maintains natural structural integrity or activity of the cellular membrane or the constituents of the cellular membrane so that the nanoparticle functions as decoy for the toxin's target cell, e.g., red blood cells. For example, the nanoparticle can retain at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the natural structural integrity for functioning as decoy for the toxin's target cell, e.g., red blood cells.

In some embodiments, the nanoparticle in the present composition is biocompatible or biodegradable. For example, the inner core of the nanoparticle comprises PLGA and the outer surface of the nanoparticle comprises a plasma membrane derived from a red blood cell.

The nanoparticle in the present composition can have any suitable half-life in vivo. For example, the nanoparticle can has a half-life in blood circulation in vivo for at least about 2-5 times of the half-life of a PEG-coated, comparable nanoparticle, or has a half-life in blood circulation in vivo for at least about 1 to about 40 hours, e.g., about 1, 2, 3, 4, 5, 6, 7, 8, 9, 10, 15, 20, 25, 30, 35 or 40 hours.

The outer surface of the nanoparticle in the present composition can comprise a synthetic membrane. In some embodiments, the nanoparticles in the present composition comprise a mixture of nanoparticles that comprise an outer surface comprising a cellular membrane and nanoparticles that comprise an outer surface comprising a synthetic membrane. The nanoparticles that comprise an outer surface comprising a synthetic membrane may or may not absorb or bind to a toxin. In some embodiments, both the nanoparticles that comprise an outer surface comprising a cellular membrane and nanoparticles that comprise an outer surface comprising a synthetic membrane absorb or bind to a toxin. In other embodiments, the nanoparticles that comprise an outer surface comprising a cellular membrane absorb or bind to a toxin, but the nanoparticles that comprise an outer surface comprising a synthetic membrane do not absorb or bind to a toxin.

The present composition can comprise the nanoparticles that comprise an outer surface comprising a cellular membrane and nanoparticles that comprise an outer surface comprising a synthetic membrane in any suitable ratio. In some embodiments, the present composition can comprise at least about 1% (w/w), 2% (w/w), 3% (w/w), 4% (w/w), 5% (w/w), 6% (w/w), 7% (w/w), 8% (w/w), 9% (w/w), 10% (w/w), 20% (w/w), 30% (w/w), 40% (w/w), 50% (w/w), 60% (w/w), 70% (w/w), 80% (w/w), 90% (w/w), 91% (w/w), 92% (w/w), 93% (w/w), 94% (w/w), 95% (w/w), 96% (w/w), 97% (w/w), 98% (w/w), 99% (w/w), or more of the nanoparticles that comprise an outer surface comprising a cellular membrane. In other embodiments, the present composition can comprise at least about 1% (w/w), 2% (w/w), 3% (w/w), 4% (w/w), 5% (w/w), 6% (w/w), 7% (w/w), 8% (w/w), 9% (w/w), 10% (w/w), 20% (w/w), 30% (w/w), 40% (w/w), 50% (w/w), 60% (w/w), 70% (w/w), 80% (w/w), 90% (w/w), 91% (w/w), 92% (w/w), 93% (w/w), 94% (w/w), 95% (w/w), 96% (w/w), 97% (w/w), 98% (w/w), 99% (w/w), or more of the nanoparticles that comprise an outer surface comprising a synthetic membrane. For example, the present composition can comprise about 1-10% (w/w) of the nanoparticles that comprise an outer surface comprising a cellular membrane and about 90-99% (w/w) of the nanoparticles that comprise an outer surface comprising a synthetic membrane, about 11-25% (w/w) of the nanoparticles that comprise an outer surface comprising a cellular membrane and about 75-89% (w/w) of the nanoparticles that comprise an outer surface comprising a synthetic membrane, about 50% (w/w) of the nanoparticles that comprise an outer surface comprising a cellular membrane and about 50% (w/w) of the nanoparticles that comprise an outer surface comprising a synthetic membrane, about 51-75% (w/w) of the nanoparticles that comprise an outer surface comprising a cellular membrane and about 49-25% (w/w) of the nanoparticles that comprise an outer surface comprising a synthetic membrane, or about 90-100% (w/w) of the nanoparticles that comprise an outer surface comprising a cellular membrane and about 0-10% (w/w) of the nanoparticles that comprise an outer surface comprising a synthetic membrane.

The cellular membrane of the outer surface of the nanoparticle in the present composition can be configured to absorb or bind to any suitable toxin. For example, the cellular membrane of the outer surface of the nanoparticle in the present composition can be configured to absorb or bind to a biological toxin. Exemplary biological toxin can be a viral, bacterial, fungal, plant or animal toxin, whether in the natural form or modified form. In some embodiments, the bacterial toxin is a toxin from a gram-positive or gram-negative bacterium, or a toxin from *E. coli* or *Staphylococcus aureus*, e.g., a toxin from a virulent strain of methicillin-resistant *S. aureus* (MRSA). In other embodiments, the fungal toxin is a toxin from *Candida albicans* or *Aspergillus fumigatus*. In still other embodiments, the animal toxin is a toxin from a reptile, e.g., a turtle, a crocodile, a snake, a lizard or a tuatara, or an arthropod, e.g., an insect, a spider or a scorpion. The animal toxin can be in any suitable form, e.g., the animal toxin be comprised in an animal venom. In yet other embodiments, the biological toxin is a pore-forming toxin, e.g., α-toxin from *Staphylococcus aureus* or a virulent strain of methicillin-resistant *S. aureus* (MRSA). In yet other embodiments, the natural target of the pore-forming toxin is a mammalian red blood cell, e.g., human red blood cell.

In some embodiments, the polymeric networks in the polymeric hydrogel and/or with the nanoparticle(s) can be crosslinked with each other in any suitable way. For example, the polymeric hydrogel can comprise polymeric networks that are either physically or covalently crosslinked with each other. In another example, the polymeric hydrogel can comprise polymeric networks that are either physically or covalently crosslinked with the nanoparticle(s). In still another example, the polymeric hydrogel can comprise polymeric networks that are either physically or covalently crosslinked with each other and the polymeric networks that are either physically or covalently crosslinked with the nanoparticle(s).

The present composition can further comprise a suitable substance, e.g., a therapeutic agent, a prophylactic agent, a diagnostic or marker agent, a prognostic agent, an isolation agent, a monitoring agent, or a combination thereof. Exemplary therapeutic agent or prophylactic agent can be an anti-viral agent, an antibiotic, an anti-fungal agent, or an anti-protozoa agent. In some embodiments, the therapeutic agent or prophylactic agent is quinine. In other embodiments, the therapeutic agent or prophylactic agent is an antibiotic. Any suitable antibiotic can be used. For example, the antibiotic can be an inhibitor of cell wall synthesis, an inhibitor of protein synthesis, an inhibitor of membrane function, an inhibitor for folate pathway, or an inhibitor of nucleic acid synthesis function. Any suitable inhibitor of cell wall synthesis can be used. For example, the inhibitor of cell wall synthesis can be penicillin, cephalosporin, monobactam, penem, a glycopeptide, or a lipoglycopeptide.

In some embodiments, the present composition can further comprise exemplary antibiotic(s), or a combination thereof, listed in the following Table 1.

TABLE 1

| Exemplary Antibiotics | |
|---|---|
| | International Common Name Examples |
| Beta-lactams (Penicillins)- Inhibitors of Cell Wall Synthesis | |
| Penicillins (pen G) | Penicillin G |
| Penicillinase-stable penicillins (pen M) | Oxacillin Methicillin |
| Aminopenicillins (pen A) | Ampicillin |
| Penicillinase labile: hydrolyzed by *staphylococcal* penicillinase | Amoxicillin |
| Carboxypenicillins (pen C) | Ticarcillin |
| Ureidopenicillins (pen U) | Piperacillin |
| Beta -lactam/Beta -lactamase inhibitor combinations | Amoxicillin + clavulanic acid Ampicillin + sulbactam Ticarcillin + clavulanic acid Piperacillin + tazobactam |
| Amidinopenicillin | Mecillinam |
| Beta-lactams (Cephems)-Inhibitors of Cell Wall Synthesis | |
| 1st Generation Cephalosporins C1G | Cephalothin Cefazolin |
| 2nd Generation Cephalosporins C2G | Cefuroxime Cefamandole Cephamycin (new C2G) Cefoxitin Cefotetan |
| 3rd Generation Cephalosporins C3G | Cefotaxime Ceftazidime Ceftriaxone |
| 4th Generation Cephalosporins C4G Oral C3G | Cefepime |

TABLE 1-continued

| Exemplary Antibiotics | |
|---|---|
| | International Common Name Examples |
| Next Generation Cephalosporins (Anti-MRSA) | Ceftobiprole Ceftaroline |
| Beta-lactams-Inhibitors of Cell Wall Synthesis | |
| Monobactams | Aztreonam |
| Penems -Carbapenems | Imipenem |
| Penems | Meropenem Etrapenem Doripenem Faropenem |
| Glycopeptides - Inhibitors of Cell Wall Synthesis | |
| Glycopeptides | Vancomycin |
| Lipoglycopeptides | Dalbavancin Oritavancin Teavanacin Teicoplanin |
| Inhibitors of Protein Synthesis | |
| Aminoglycosides - (Bactericidal) | Gentamicin Streptomycin Tobramycin Kanamycin Amikacin |
| Macrolide-lincosamide-streptogramin-ketolide- (MLSK) (Bacteriostatic) | Erythromycin Clindamycin Quinupristin-Dalfopristin (Synercid) Clarithromycin Azithromycin Telithromycin |
| Tetracyclines - (Bacteriostatic) | Tetracycline Doxycycline Minocycline |
| Glycylcyclines | Tigecycline |
| Phenocols (Bacteriostatic) | Chloramphenicol |
| Oxazolidinones (Bactericidal for *Streptococci*; Bacteriostatic for *Enterococcus* and *Staphylococci*) | Linezolid |
| Ansamycins ((Bacteriostatic or Bactericidal depending on organism and concentration) | Rifampin |
| Inhibitors of Membrane Function | |
| Lipopeptides | Polymyxin B Colistin |
| Cyclic Lipopeptides | Daptomycin |
| Antimetabolites- Folate Pathway Inhibitors | |
| Sulfonamides (Bactericidal)- Inhibits pteridine synthase and dihydrofolic acid reductase | Trimethoprim/ Sulfamethoxazole |
| Inhibitors of Nucleic Acid Synthesis Function | |
| Fluoroquinolones (Bactericidal)- Inhibits DNA Gyrase and Topoisomerase | Ciprofloxacin Levofloxacin Gatifloxacin Moxifloxacin Garenoxacin Lomefloxacin Norfloxacin Sparfloxacin |
| Quinolones First Generation- Narrow spectrum (Only gram negatives) | Nalidixic Acid Cinoxacin |
| Furanes (Bactericidal)- Gram positive and gram negative urinary tract infections | Nitrofurantoin |

(Adapted from Biomerieux Vitek 2 Customer Education March 2008- <http://www-.biomerieux-usa.com/upload/VITEK-Bus-Module-1-Antibiotic-Classification-and-Modes-of-Action-1.pdf>).

The therapeutic agent, the prophylactic agent, the diagnostic or marker agent, the prognostic agent, the isolation agent, the monitoring agent, or a combination thereof, can be comprised in any suitable location of the present composition. For example, the therapeutic agent, the prophylactic agent, the diagnostic or marker agent, the prognostic agent, the isolation agent, the monitoring agent, or a combination thereof, can be comprised in the nanoparticle. In some embodiments, the therapeutic agent, the prophylactic agent, the diagnostic or marker agent, the prognostic agent, the isolation agent, the monitoring agent, or a combination thereof, can be comprised in a releasable cargo in the nanoparticle. The nanoparticle can comprise a releasable cargo at any suitable location. For example, the releasable cargo can be located within or on the inner core, between the inner core and the outer surface, or within or on the outer surface. The release of the releasable cargo can be triggered by any suitable mechanisms. For example, the release of the releasable cargo can be triggered by a contact between the nanoparticle and the subject or cells of the subject, or by a change of a physical parameter surrounding the nanoparticle. The nanoparticle can comprise any suitable type of a releasable cargo. For example, the releasable cargo can be a metallic particle, a polymeric particle, a dendrimer particle, or an inorganic particle. In some embodiments, the therapeutic agent, the prophylactic agent, the diagnostic or marker agent, the prognostic agent, the isolation agent, the monitoring agent, or a combination thereof, can be comprised in the present composition but outside the nanoparticle.

The present composition can be made, stored, transported and/or used in any suitable formulation. In some embodiments, the present composition can further comprise a pharmaceutically acceptable carrier or excipient. In other embodiments, the present composition can be comprised in a medicament delivery system, a medical device or a consumer product. Any suitable medicament delivery system or medical device can be used. For example, the medicament delivery system or the medical device can be an implant, e.g., breast implant or an implant placed during or after bone surgery, a catheter, a sustained-release drug delivery system, or a dressing for healing of burn or other hard-to-heal wound. The present composition can be made, stored, transported and/or used in any suitable consumer product. For example, the consumer product can be a hygiene product, e.g., a disposable diaper. In still other embodiments, the present composition can be configured to be a part of scaffolds in tissue engineering.

The present composition can be configured for any suitable route of administration. For example, the present composition can be configured for rectal, nasal, topical, ocular, intramuscular, intraperitoneal, or subcutaneous route of administration.

In some embodiments, the present composition can be configured as a toxin-neutralizing antimicrobial hydrogel. The toxin-neutralizing antimicrobial hydrogel can be configured for topical application in an infected area. The toxin-neutralizing antimicrobial hydrogel can also be coated on a medical device, e.g., a medical device configured for therapeutic or prophylactic administration.

In another aspect, the present invention provides for use of an effective amount of the above composition for the manufacture of a medicament for decreasing or neutralizing the effect of a toxin, or for treating or preventing an infection by a microbe that produces a toxin, in a subject. The present invention also provides for the manufactured medicament.

In still another aspect, the present invention provides for a method of preserving therapeutic functionality of a toxin-absorbing or binding nanoparticle, which method comprises impregnating a toxin-absorbing or binding nanoparticle in a polymeric hydrogel to form a composition comprising said polymeric hydrogel impregnated with said toxin-absorbing or binding nanoparticle, wherein said nanoparticle comprises a) an inner core comprising a non-cellular material, and b) an outer surface comprising a cellular membrane configured for absorbing or binding said toxin. The nanoparticle and the polymeric hydrogel are as described above. The present invention also provides for a manufactured composition wherein the therapeutic functionality of a toxin-absorbing or binding nanoparticle is preserved.

In some embodiments, the hydrogel in the composition can comprise poly(ethylene glycol) dimethacrylate (PEGDMA). In other embodiments, the cellular membrane of the nanoparticle in the composition can comprise a plasma membrane derived from a red blood cell. In still other embodiments, the present methods can further comprise adding an antibiotic to the composition. The antibiotic can be comprised in any suitable part of the composition, e.g., the nanoparticle. The antibiotic can be comprised in any suitable part of the nanoparticle, e.g., a releasable cargo of the nanoparticle. The present invention also provides for a manufactured composition wherein the therapeutic functionality of a toxin-absorbing or binding nanoparticle is preserved.

C. Methods for Decreasing or Neutralizing the Effect of a Toxin, or Treating or Preventing an Infection in a Subject In still another aspect, the present invention provides for a method for decreasing or neutralizing the effect of a toxin, or for treating or preventing an infection by a microbe that produces a toxin, in a subject, which method comprises administering, to a subject in need, or to cells of said subject, an effective amount of a composition or medicament described in the above Section B.

The present methods can be used to decrease or neutralize the effect of a toxin, or treat or prevent an infection in any suitable subject. In some embodiments, the subject is a mammal. In some embodiments, the mammal is a human. In other embodiments, the mammal is a non-human mammal, including a pet, a farm animal, an economic animal, a sport animal and an experimental animal, such as a cat, a dog, a horse, a cow, an ox, a pig, a donkey, a sheep, a lamb, a goat, a mouse, a rabbit, a primate, including a monkey and a chimpanzee.

In some embodiments, the present methods can be used for decreasing the effect of a toxin in the subject. In other embodiments, the present methods can be used for neutralizing the effect of a toxin in the subject. In still other embodiments, the present methods can be used for treating an infection by a microbe that produces a toxin in the subject. In yet other embodiments, the present methods can be used for preventing an infection by a microbe that produces a toxin in the subject.

In some embodiments, the composition used in the present methods, especially the nanoparticle in the present composition, substantially lacks immunogenicity to the subject, e.g., a mammal. For example, the cellular membrane can be derived from a cell, e.g., a red blood cell, from the same species of the mammal. In another example, the mammal is a human and the cellular membrane is derived from a human cell, e.g., a human red blood cell. In some embodiments, the cellular membrane can be derived from a cell, e.g., a red blood cell, of the mammal to be treated. For example, the cellular membrane can be derived from a red blood cell of the human to be treated.

The composition used in the present methods can comprise any suitable polymeric hydrogel. In some embodiments, the polymeric hydrogel can comprise a material selected from the group consisting of poly(ethylene glycol) dimethacrylate (PEGDMA), silicone, gelatin, chitosan, alginate, polyester, poly(vinyl alcohol) and polyacrylamide, polyethylene oxide, polyvinyl alcohol, Carbopol®, polyacrylamidomethylpropanesulfonate, polyacrylic acid, a salt of acrylic acid (including sodium and sulfopropyl acrylate, 2-hydroxyethyl methacrylate), agarose, methylcellulose, hyaluronan, and copolymers thereof. In a specific example, the polymeric hydrogel can comprise poly(ethylene glycol) dimethacrylate (PEGDMA).

During use, the polymeric hydrogel in the composition used in the present methods can be in hydrated form. For example, during use, the polymeric hydrogel in the present composition can comprise at least about 1% (w/w), 2% (w/w), 3% (w/w), 4% (w/w), 5% (w/w), 6% (w/w), 7% (w/w), 8% (w/w), 9% (w/w), 10% (w/w), 20% (w/w), 30% (w/w), 40% (w/w), 50% (w/w), 60% (w/w), 70% (w/w), 80% (w/w), 90% (w/w), 91% (w/w), 92% (w/w), 93% (w/w), 94% (w/w), 95% (w/w), 96% (w/w), 97% (w/w), 98% (w/w), 99% (w/w), or more of water content.

The polymeric hydrogel in the composition used in the present methods can possess any suitable degree of flexibility. In some embodiments, the polymeric hydrogel can possess a degree of flexibility suitable to be applied to a tissue or an organ. In other embodiments, the polymeric hydrogel can possess a degree of flexibility suitable to be applied to a natural tissue or a natural organ.

The nanoparticle in the composition used in the present methods can comprise any suitable inner core. For example, the inner core of the nanoparticle can comprise a polymeric particle core, a silica particle core, or a metal, e.g., gold, particle core. Any suitable polymeric particle core can be used. In some embodiments, the polymeric particle core can comprise an optical shift property. In other embodiments, the polymeric particle core can comprise a metal, e.g., gold, iron oxide or a quantum dot. In still other embodiments, the inner core of the nanoparticle can comprise a biocompatible or a synthetic material, such as poly(lactic-c-glycolic acid) (PLGA), polylactic acid (PLA), polyglycolic acid (PGA), polycaprolactone (PCL), polylysine, and polyglutamic acid. In yet other embodiments, the inner core of the nanoparticle supports the outer surface.

The nanoparticle in the composition used in the present methods can comprise a cellular membrane derived from any suitable cell that is a target or that absorbs or binds to a toxin. For example, the nanoparticle can comprise a plasma membrane or an intracellular membrane derived from a cell that is a target or that absorbs or binds to a toxin. The nanoparticle can comprise any suitable cellular membrane derived from a red blood cell. For example, the nanoparticle can comprise a plasma membrane or an intracellular membrane derived from a red blood cell. In some embodiments, the cellular membrane comprises a plasma membrane derived from a red blood cell, a lymphocyte or a platelet, e.g., a plasma membrane derived from a human red blood cell, lymphocyte or platelet. In some embodiments, the nanoparticle can comprise any suitable naturally occurring cellular membrane derived from a red blood cell, a lymphocyte or a platelet. In some embodiments, the cellular membrane comprises a naturally occurring plasma membrane derived from a red blood cell, a lymphocyte or a platelet, e.g., a naturally occurring plasma membrane derived from a human red blood cell, lymphocyte or platelet. In some embodiments, the cellular membrane of the nanoparticle comprises membrane-bound proteins or glycans.

The nanoparticle in the composition used in the present methods can have any suitable size. For example, the nanoparticle can have a diameter from about 10 nm to about 10 μm. In certain embodiments, the diameter of the nanoparticle is about 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 200 nm, 300 nm, 400 nm, 500 nm, 600 nm, 700 nm, 800 nm, 900 nm, 1 μm, 2 μm, 3 μm, 4 μm, 5 μm, 6 μm, 7 μm, 8 μm, 9 μm, and 10 μm.

The nanoparticle in the composition used in the present methods can have any suitable shape, including but not limited to, sphere, square, rectangle, triangle, circular disc, cube-like shape, cube, rectangular parallelepiped (cuboid), cone, cylinder, prism, pyramid, right-angled circular cylinder and other regular or irregular shape.

In some embodiments, the nanoparticle in the composition used in the present methods substantially lacks constituents of the cell, e.g., red blood cell, from which the cellular membrane is derived. For example, the nanoparticle can lack at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the constituents of the cell, e.g., the red blood cell, from which the cellular membrane is derived. In some embodiments, the nanoparticle comprises a plasma membrane derived from a red blood cell and the nanoparticle substantially lacks hemoglobin. For example, the nanoparticle can lack at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the hemoglobin.

In some embodiments, the nanoparticle in the composition used in the present methods substantially maintains natural structural integrity or activity of the cellular membrane or the constituents of the cellular membrane so that the nanoparticle functions as decoy for the toxin's target cell, e.g., red blood cells. For example, the nanoparticle can retain at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the natural structural integrity for functioning as decoy for the toxin's target cell, e.g., red blood cells.

In some embodiments, the nanoparticle in the composition used in the present methods is biocompatible or biodegradable. For example, the inner core of the nanoparticle comprises PLGA and the outer surface of the nanoparticle comprises a plasma membrane derived from a red blood cell.

The nanoparticle in the composition used in the present methods can have any suitable half-life in vivo. For example, the nanoparticle can has a half-life in blood circulation in vivo for at least about 2-5 times of the half-life of a PEG-coated, comparable nanoparticle, or has a half-life in blood circulation in vivo for at least about 1 to about 40 hours, e.g., about 1, 2, 3, 4, 5, 6, 7, 8, 9, 10, 15, 20, 25, 30, 35 or 40 hours.

The outer surface of the nanoparticle in the composition used in the present methods can further comprise a synthetic membrane. In some embodiments, the nanoparticles in the composition used in the present methods comprise a mixture of nanoparticles that comprise an outer surface comprising a cellular membrane and nanoparticles that comprise an outer surface comprising a synthetic membrane. The nanoparticles that comprise an outer surface comprising a synthetic membrane may or may not absorb or bind to a toxin. In some embodiments, both the nanoparticles that comprise an outer surface comprising a cellular membrane and nanoparticles that comprise an outer surface comprising a synthetic membrane absorb or bind to a toxin. In other embodiments, the nanoparticles that comprise an outer surface comprising a cellular membrane absorb or bind to a toxin, but the nanoparticles that comprise an outer surface comprising a synthetic membrane do not absorb or bind to a toxin.

The composition used in the present methods can comprise the nanoparticles that comprise an outer surface comprising a cellular membrane and nanoparticles that comprise an outer surface comprising a synthetic membrane in any suitable ratio. In some embodiments, the present composition can comprise at least about 1% (w/w), 2% (w/w), 3% (w/w), 4% (w/w), 5% (w/w), 6% (w/w), 7% (w/w), 8% (w/w), 9% (w/w), 10% (w/w), 20% (w/w), 30% (w/w), 40% (w/w), 50% (w/w), 60% (w/w), 70% (w/w), 80% (w/w), 90% (w/w), 91% (w/w), 92% (w/w), 93% (w/w), 94% (w/w), 95% (w/w), 96% (w/w), 97% (w/w), 98% (w/w), 99% (w/w), or more of the nanoparticles that comprise an outer surface comprising a cellular membrane. In other embodiments, the present composition can comprise at least about 1% (w/w), 2% (w/w), 3% (w/w), 4% (w/w), 5% (w/w), 6% (w/w), 7% (w/w), 8% (w/w), 9% (w/w), 10% (w/w), 20% (w/w), 30% (w/w), 40% (w/w), 50% (w/w), 60% (w/w), 70% (w/w), 80% (w/w), 90% (w/w), 91% (w/w), 92% (w/w), 93% (w/w), 94% (w/w), 95% (w/w), 96% (w/w), 97% (w/w), 98% (w/w), 99% (w/w), or more of the nanoparticles that comprise an outer surface comprising a synthetic membrane. For example, the composition used in the present methods can comprise about 1-10% (w/w) of the nanoparticles that comprise an outer surface comprising a cellular membrane and about 90-99% (w/w) of the nanoparticles that comprise an outer surface comprising a synthetic membrane, about 11-25% (w/w) of the nanoparticles that comprise an outer surface comprising a cellular membrane and about 75-89% (w/w) of the nanoparticles that comprise an outer surface comprising a synthetic membrane, about 50% (w/w) of the nanoparticles that comprise an outer surface comprising a cellular membrane and about 50% (w/w) of the nanoparticles that comprise an outer surface comprising a synthetic membrane, about 51-75% (w/w) of the nanoparticles that comprise an outer surface comprising a cellular membrane and about 49-25% (w/w) of the nanoparticles that comprise an outer surface comprising a synthetic membrane, or about 90-100% (w/w) of the nanoparticles that comprise an outer surface comprising a cellular membrane and about 0-10% (w/w) of the nanoparticles that comprise an outer surface comprising a synthetic membrane.

The present methods can be used to absorb or bind to any suitable toxin. For example, the nanoparticle in the composition used in the present methods can be configured to absorb or bind to a biological toxin. Exemplary biological toxin can be a viral, bacterial, fungal, plant or animal toxin, whether in the natural form or modified form. In some embodiments, the bacterial toxin is a toxin from a gram-positive or gram-negative bacterium, or a toxin from *E. coli* or *Staphylococcus aureus*, e.g., a toxin from a virulent strain of methicillin-resistant *S. aureus* (MRSA). In other embodiments, the fungal toxin is a toxin from *Candida albicans* or *Aspergillus fumigatus*. In still other embodiments, the animal toxin is a toxin from a reptile, e.g., a turtle, a crocodile, a snake, a lizard or a tuatara, or an arthropod, e.g., an insect, a spider or a scorpion. The animal toxin can be in any suitable form, e.g., the animal toxin be comprised in an animal venom. In yet other embodiments, the biological toxin is a pore-forming toxin, e.g., $\alpha$-toxin from *Staphylococcus aureus* or a virulent strain of methicillin-resistant *S. aureus* (MRSA). In yet other embodiments, the natural target of the pore-forming toxin is a mammalian red blood cell, e.g., human red blood cell.

In some embodiments, the polymeric networks in the polymeric hydrogel and/or the nanoparticle(s) in the composition used in the present methods can be crosslinked with each other in any suitable way. For example, the polymeric hydrogel can comprise polymeric networks that are either physically or covalently crosslinked with each other. In another example, the polymeric hydrogel can comprise polymeric networks that are either physically or covalently crosslinked with the nanoparticle(s). In still another example, the polymeric hydrogel can comprise polymeric networks that are either physically or covalently crosslinked with each other and the polymeric networks that are either physically or covalently crosslinked with the nanoparticle(s).

The present methods can comprise administering an additional suitable substance, e.g., a therapeutic agent, a prophylactic agent, a diagnostic or marker agent, a prognostic agent, an isolation agent, a monitoring agent, or a combination thereof, to the subject. Exemplary therapeutic agent or prophylactic agent can be an anti-viral agent, an antibiotic, an anti-fungal agent, or an anti-protozoa agent. In some embodiments, the therapeutic agent or prophylactic agent is quinine. In other embodiments, the therapeutic agent or prophylactic agent is an antibiotic. Any suitable antibiotic can be used. For example, the antibiotic can be an inhibitor of cell wall synthesis, an inhibitor of protein synthesis, an inhibitor of membrane function, an inhibitor for folate pathway, or an inhibitor of nucleic acid synthesis function. Any suitable inhibitor of cell wall synthesis can be used. For example, the inhibitor of cell wall synthesis can be penicillin, cephalosporin, monobactam, penem, a glycopeptide, or a lipoglycopeptide.

In some embodiments, the methods can further comprise administering, to a subject, an exemplary antibiotic(s), or a combination thereof, as listed in the above Table 1.

The therapeutic agent, the prophylactic agent, the diagnostic or marker agent, the prognostic agent, the isolation agent, the monitoring agent, or a combination thereof, can be comprised in any suitable location in the composition used in the present methods. For example, the therapeutic agent, the prophylactic agent, the diagnostic or marker agent, the prognostic agent, the isolation agent, the monitoring agent, or a combination thereof, can be comprised in the nanoparticle. In some embodiments, the therapeutic agent, the prophylactic agent, the diagnostic or marker agent, the prognostic agent, the isolation agent, the monitoring agent, or a combination thereof, can be comprised in a releasable cargo in the nanoparticle. The nanoparticle can comprise a releasable cargo at any suitable location. For example, the releasable cargo can be located within or on the inner core, between the inner core and the outer surface, or within or on the outer surface. The release of the releasable cargo can be triggered by any suitable mechanisms. For example, the release of the releasable cargo can be triggered by a contact between the nanoparticle and the subject or cells of the subject, or by a change of a physical parameter surrounding the nanoparticle. The nanoparticle can comprise any suitable type of a releasable cargo. For example, the releasable cargo can be a metallic particle, a polymeric particle, a dendrimer particle, or an inorganic particle. In some embodiments, the therapeutic agent, the prophylactic agent, the diagnostic or marker agent, the prognostic agent, the isolation agent, the monitoring agent, or a combination thereof, can be comprised in the composition used in the present methods but outside the nanoparticle. In other embodiments, the therapeutic agent, the prophylactic agent, the diagnostic or marker agent, the prognostic agent, the isolation agent, the monitoring agent, or a combination thereof, can be administered to the subject separately from the composition used in the present methods. The composition used in the present methods and the additional substance can be administered to the subject simultaneously or sequentially.

In some embodiments, the present methods can further comprise administering a pharmaceutically acceptable carrier or excipient to the subject.

The composition used in the present methods can be administered using any suitable delivery mechanisms or techniques. In some embodiments, the composition can be administered alone. In other embodiments, the composition can be administered with a pharmaceutically acceptable carrier or excipient. In still other embodiments, the composition can be administered via a medicament delivery system, a medical device or a consumer product. Any suitable medicament delivery system or medical device can be used. For example, the medicament delivery system or the medical device can be an implant, e.g., breast implant or an implant placed during or after bone surgery, a catheter, a sustained-release drug delivery system, or a dressing for healing of burn or other hard-to-heal wound. In another example, the consumer product can be a hygiene product, e.g., a disposable diaper. In still another example, the present methods can be used in tissue engineering by including the present composition in scaffolds in tissue engineering.

The composition used in the present methods can be administered to the subject via any suitable route of administration. In some embodiments, the composition can be administrated to the subject via rectal, nasal, topical, ocular, intramuscular, intraperitoneal, or subcutaneous route of administration.

In an example, the composition can be administrated to the subject via topical route of administration. The hydrogel in the composition can comprise poly(ethylene glycol) dimethacrylate (PEGDMA). The cellular membrane of the nanoparticle in the composition can comprise a plasma membrane derived from a red blood cell. The present methods can further comprise administering an antibiotic to the subject. The antibiotic can be comprised in any suitable part of the composition, e.g., the nanoparticle. The antibiotic can be comprised in any suitable part of the nanoparticle, e.g., a releasable cargo of the nanoparticle.

D. Pharmaceutical Compositions and Administration Routes

The pharmaceutical compositions comprising the nanoparticles, alone or in combination with other active ingredient(s), described herein may further comprise one or more pharmaceutically-acceptable excipients. A pharmaceutically-acceptable excipient is a substance that is non-toxic and otherwise biologically suitable for administration to a subject. Such excipients facilitate administration of the nanoparticles, alone or in combination with other active ingredient(s), described herein and are compatible with the active ingredient. Examples of pharmaceutically-acceptable excipients include stabilizers, lubricants, surfactants, diluents, anti-oxidants, binders, coloring agents, bulking agents, emulsifiers, or taste-modifying agents. In preferred embodiments, pharmaceutical compositions according to the various embodiments are sterile compositions. Pharmaceutical compositions may be prepared using compounding techniques known or that become available to those skilled in the art.

Sterile compositions are within the present disclosure, including compositions that are in accord with national and local regulations governing such compositions.

The pharmaceutical compositions and the nanoparticles, alone or in combination with other active ingredient(s), described herein may be formulated as solutions, emulsions, suspensions, or dispersions in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. The nanoparticles, alone or in combination with other active ingredient(s), described herein, and preferably in the form of a pharmaceutical composition, may be administered by a suitable route of delivery, such as oral, parenteral, rectal, nasal, topical, or ocular routes, or by inhalation. In some embodiments, the compositions are formulated for intravenous or oral administration.

For oral administration, the nanoparticles, alone or in combination with another active ingredient, may be provided in a solid form, such as a tablet or capsule, or as a solution, emulsion, or suspension. To prepare the oral compositions, the nanoparticles, alone or in combination with other active ingredient(s), may be formulated to yield a dosage of, e.g., from about 0.01 to about 50 mg/kg daily, or from about 0.05 to about 20 mg/kg daily, or from about 0.1 to about 10 mg/kg daily. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinylpyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil, such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The compositions may be formulated for rectal administration as a suppository. For parenteral use, including intravenous, intramuscular, intraperitoneal, intranasal, or subcutaneous routes, the nanoparticles, alone or in combination with other active ingredient(s), may be provided in sterile aqueous solutions or suspensions, buffered to an appropriate pH and isotonicity or in parenterally acceptable oil. Suitable aqueous vehicles can include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 μg/kg/minute of agent admixed with a pharmaceutical carrier over a period ranging from several minutes to several days.

For nasal, inhaled, or oral administration, the nanoparticles, alone or in combination with other active ingredient(s), may be administered using, for example, a spray formulation also containing a suitable carrier.

For topical applications, the nanoparticles, alone or in combination with other active ingredient(s), are preferably formulated as creams or ointments or a similar vehicle suitable for topical administration. For topical administration, the nanoparticles, alone or in combination with other active ingredient(s), may be mixed with a pharmaceutical carrier at a concentration of about 0.1% to about 10% of drug to vehicle. Another mode of administering the nanoparticles, alone or in combination with other active ingredient(s), may utilize a patch formulation to effect transdermal delivery.

In certain embodiments, the present disclosure provides pharmaceutical composition comprising the nanoparticles, alone or in combination with other active ingredient(s), and methylcellulose. In certain embodiments, methylcellulose is in a suspension of about 0.1, 0.2, 0.3, 0.4, or 0.5 to about 1%. In certain embodiments, methylcellulose is in a suspension of about 0.1 to about 0.5, 0.6, 0.7, 0.8, 0.9, or 1%. In certain embodiments, methylcellulose is in a suspension of about 0.1 to about 1%. In certain embodiments, methylcellulose is in a suspension of about 0.1, 0.2, 0.3, 0.4, 0.5, 0.6, 0.7, 0.8, 0.8, or 1%. In certain embodiments, methylcellulose is in a suspension of about 0.5%.

E. Exemplary Embodiments

In some embodiments, the present invention provides a composition comprising toxin-absorbing nanoparticles and methods of use thereof, for topical treatment of infected areas, as well as antimicrobial coatings on implantable devices. The present invention further provides methods of preserving therapeutic nanoparticle functionalities via hydrogel.

In certain embodiments, the present invention provides that the composition is an antimicrobial hydrogels endowed with toxin-neutralizing capacity via the incorporation of toxinabsorbing nanoparticles, such antimicrobial hydrogels can soak up and/or eliminate the toxins produced by infectious microbes. In certain embodiment, such antimicrobial hydrogels with toxin-absorbing nanoparticles are nanosponges. In other embodiments, the composition of the invention comprises deformable hydrogels which can be used to enable delivery of sustained, local levels of antibiotic to reduce toxin problems for current standard of care, involving bolus dosing.

In some embodiments, the present invention further provides methods of treating infections by administering to a subject in need an effective amount of the inventive composition comprising toxin-absorbing nanoparticles. The administration route includes, but not limited to topical administration at the infected areas. The invention further provides methods of use the inventive composition comprising toxin-absorbing nanoparticles as antimicrobial coatings for prophylactic and/or therapeutic administration on medical devices including, but not limited to, orthopedic implants and catheters.

In some embodiments, the present invention provides antimicrobial hydrogels endowed with toxin-neutralizing capacity via the incorporation of toxin-absorbing nanoparticles. In other embodiments, the present invention further provides that the antimicrobial hydrogels of the invention can be used for topical application in infected areas or for prophylactic administrations on medical devices including orthopedic implants and catheters. Methods of preserving therapeutic nanoparticle functionalities via hydrogel formulations are also provided.

Figure 2A:
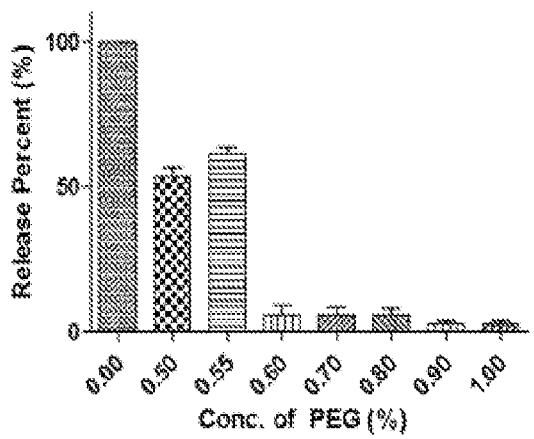
FIG. 2A illustrates a release of nanosponges from hydrogels with different PEG concentrations. Hydrogles with PEG percent higher than 0.6 vol % could reserve about 95% nanosponges after 24 h.
Figure 2B:
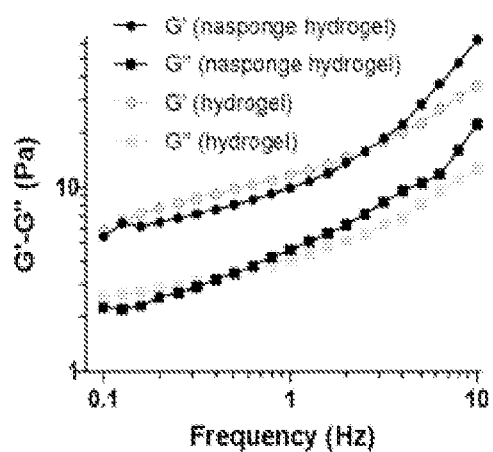
FIG. 2B illustrates a rheological characterization of different hydrogels. For each gel, its G' was higher than its G", suggesting the gelation of both gels.
Figure 2C:
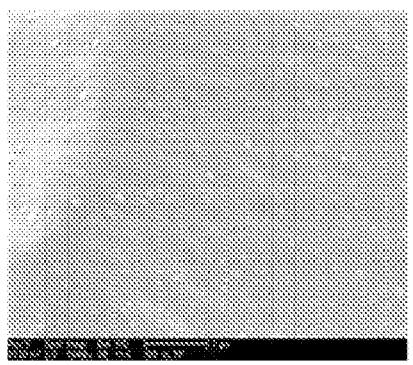
FIG. 2C illustrates a SEM image of nanosponge hydrogels.

In one embodiment of the invention, it is demonstrated that a poly(ethylene glycol) dimethacrylate (PEGDMA) hydrogel formulation is embedded with a red blood cell membrane coated nanoparticle platform (FIG. 1). By tuning the percentage of PEG in the formulation, dense yet hydrate matrices that retains nanoparticles with varying efficiencies can be prepared (FIG. 2a). For instance, a hydrogel formulation containing 0.6 vol % of PEG was shown to retain 95% of the RBC membrane coated nanoparticles by 24 h. Nanoparticle incorporation did not interfere with the hydrogel formation, as gelation was confirmed using rheological characterizations (FIG. 2b). Scanning electron microscopy visualization also verified the presence of nanoparticles in the hydrogel formulation (FIG. 2c).

Figure 3:
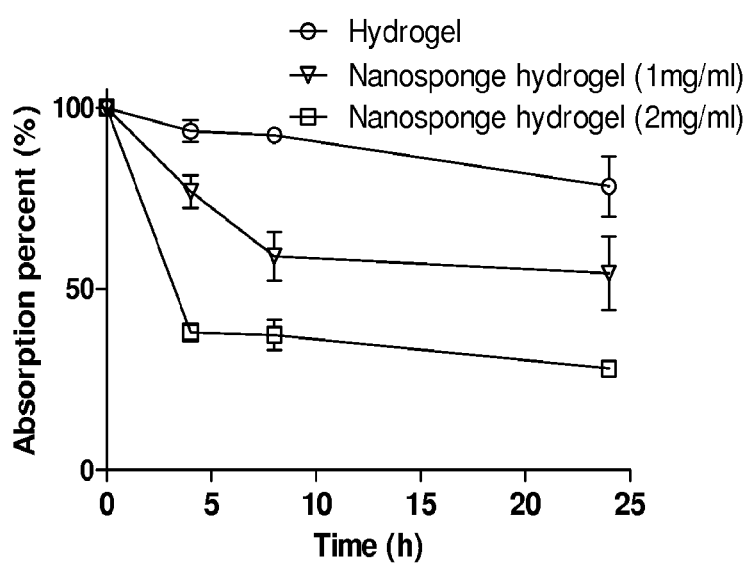
FIG. 3 illustrates absorption of α-toxin by hydrogels with different concentrations of nanosponge. 0.5 ml α-toxin solution (10 μg/ml) was added onto 0.5 ml hydrogels with nanosponge concentration of 2, 1 or 0 mg/ml. All tubes with α-toxin and hydrogels were put into a 37° C. shaking incubator. 40 μl supernatants were taken out at different times and the concentration of α-toxin in supernatants was detected using ELISA method. For hydrogels with no nanosponge, only 22% α-toxin diffused into the gel after 24 h, while 46% and 72% α-toxin was absorbed by hydrogels with nanosponge concentration of 1 and 2 mg/ml, respectively.
Figure 4:
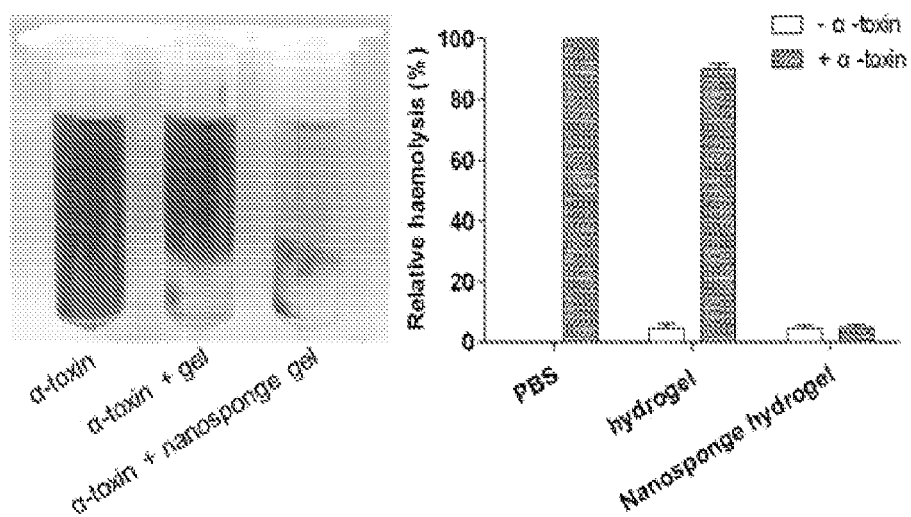
FIG. 4 illustrates centrifuged RBCs after incubation with α-toxin mixed in PBS, hydrogels, or nanosponge-loaded hydrogels.
Figure 5:
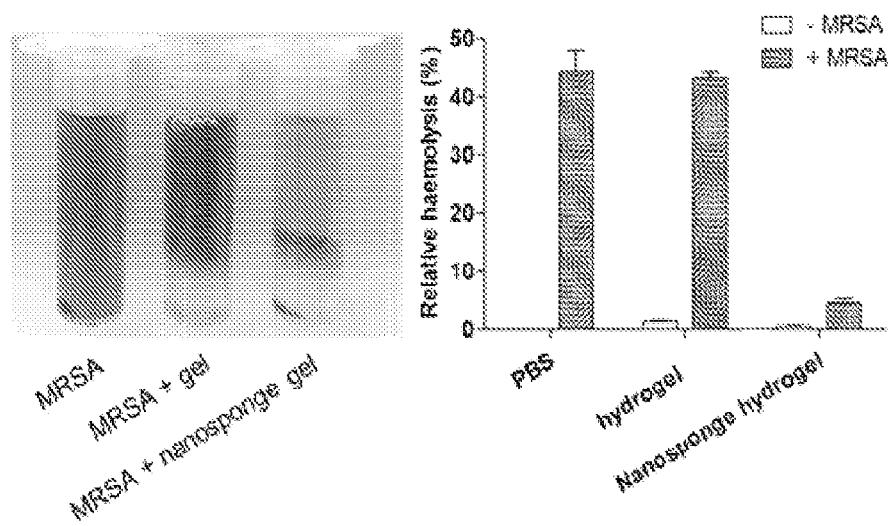
FIG. 5 illustrates centrifuged RBCs after incubation with MRSA mixed in PBS, hydrogels or nanosponge-loaded hydrogels. MRSA were cultured in liquid TSB for 24 h. Then TSB with MRSA in it was mixed with PBS, hydrogels or nanosponge-loaded hydrogels (2 mg/ml) using vortex. Fresh blood was then added and all samples were incubated in a 37° C. shaking incubator for 2 h.
Figure 6A:
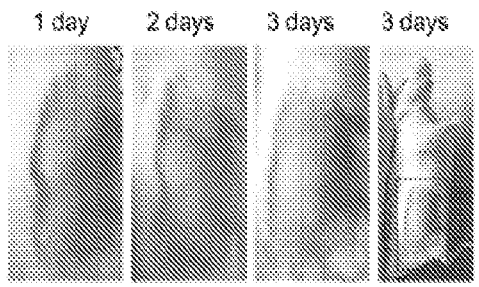
FIGS. 6A-6F illustrate an in vivo toxin neutralization. Mice were s.c. injected with α-toxin/nanosponge hydrogel or α-toxin/hydrogel.
Figure 6B:
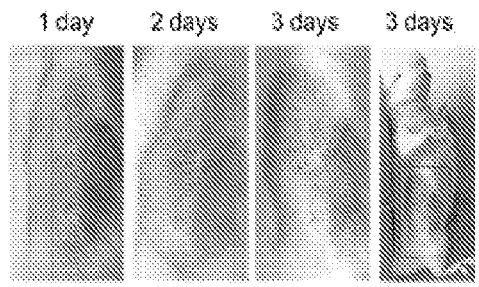
Figure 6C:
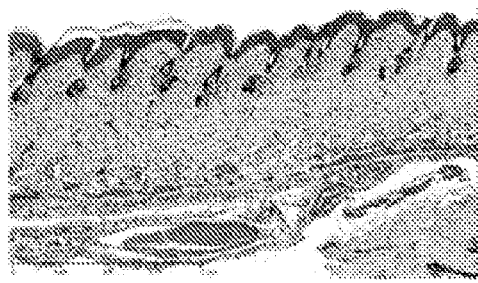
Figure 6D:
Figure 6E:
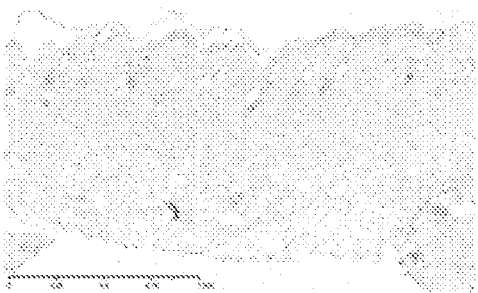
Figure 6F:

In another embodiment of the invention, it is demonstrated that by incorporated the RBC membrane coated nanoparticles, the hydrogel formulation is endowed with the ability to absorb α-toxin, a major membrane-damaging toxin secreted by *Staphylococcus aureus* (FIG. 3). Absorption efficiency was found to correlate with the amount of embedded nanoparticles, which indicates that the toxin-absorption capacity of the nanoparticles is persevered in the hydrogel. Hemolysis experiments by mixing RBCs with the toxin-neutralizing hydrogels also demonstrate that the absorbed toxins are completely neutralized (FIGS. 4a and b). Such toxin neutralization was specific to the hydrogel formulation doped with the RBC membrane coated nanoparticles. The anti-virulence effect of the hydrogel can also be applied to bacteria. Upon mixing the hydrogels with a α-toxin-secreting strain of methicillin-resistant *Staphylococcus aureus* (MRSA), the toxin-neutralizing hydrogel was found to greatly inhibit MRSA-induced hemolysis (FIGS. 5a and b). Application of the toxin-neutralizing hydrogel was also demonstrated in vivo. Subcutaneous injections of α-toxin mixtures with different hydrogel formulations revealed the beneficial effect of toxin-neutralizing hydrogel. Whereas the normal PEGDMA hydrogel failed to eliminate the necrotizing effect of the α-toxin, the nanoparticle-doped hydrogel completely removed the toxin's virulence effect, leaving the injection site unharmed by the bacterial toxin (FIG. 6).

Exemplary Application

Exemplary applications of the toxin-neutralizing antimicrobial hydrogels include but are not limited to topical administrations to treat local infections and coatings on implantable devices (e.g., catheters and prosthesis) to prevent infections associated with surgical procedures.

Exemplary Hydrogel Compositions

In some embodiments, a hydrogel consisting of PEGDMA was used to demonstrate the toxin-neutralizing hydrogel. Hydrogel formulations include, but are not limited to silicone, gelatin, chitosan, alginate, polyesters, poly(vinyl alcohol) and polyacrylamide, polyethylene oxide, polyvinyl alcohol, Carbopol®, polyacrylamidomethylpropanesulfonate, polyacrylic acid, salts of acrylic acid (including sodium and sulfopropyl acrylates, 2-hydroxyethyl methacrylate), and copolymers thereof.

Exemplary Nanoparticle Composition

In some embodiments, a red blood cell membrane coated PLGA nanoparticle is used to demonstrate the incorporation of toxin-neutralizing nanoparticles in the hydrogel formulation. Nanoparticles can comprise or consist of any core materials including but not limited to polymeric nanoparticles, silica nanoparticles, silica nanoparticles, and gold nanoparticles. Materials for nanoparticle coating includes but is not limited to biologically derived or synthetically prepared lipid membranes.

The present invention is further illustrated by the following exemplary embodiments:

1. A composition comprising a polymeric hydrogel impregnated with toxin-absorbing nanoparticles.
2. The composition of embodiment 1, wherein said polymeric hydrogel is selected from the group consisting of poly(ethylene glycol) dimethacrylate (PEGDMA), silicone, gelatin, chitosan, alginate, polyesters, poly(vinyl alcohol) and polyacrylamide, polyethylene oxide, polyvinyl alcohol, Carbopol®, polyacrylamidomethylpropanesulfonate, polyacrylic acid, salts of acrylic acid (including sodium and sulfopropyl acrylates, 2-hydroxyethyl methacrylate), and copolymers thereof.
3. The composition of embodiment 1, wherein said polymeric hydrogel is poly(ethylene glycol) dimethacrylate (PEGDMA).
4. The composition of embodiment 1, wherein said nanoparticles comprise a core material coated with biologically derived or synthetically prepared lipid membranes.
5. The composition of embodiment 4, wherein said core material is selected from the group consisting of polymeric nanoparticles, silica nanoparticles, silica nanoparticles, and gold nanoparticles.
6. The composition of embodiment 4, wherein said biologically derived lipid membrane is derived from red blood cell membrane.
7. The composition of embodiment 1, wherein said composition further comprises antibiotics.
8. The composition of embodiment 7, wherein said antibiotics are selected from the group consisting of inhibitors of cell wall synthesis, inhibitors of protein synthesis, inhibitors of membrane function, inhibitors for folate pathway, and inhibitors of nucleic acid synthesis function.
9. The composition of embodiment 8, wherein said inhibitors of cell wall synthesis are penicillins, cephalosporins, monobactams, penems, glycopeptides, or lipoglycopeptides.
10. The composition of embodiment 1, wherein said composition is toxin-neutralizing antimicrobial hydrogels.
11. The composition of embodiment 10, wherein said toxin-neutralizing antimicrobial hydrogels are used for topical application in infected areas.
12. The composition of embodiment 10, wherein said toxin-neutralizing antimicrobial hydrogels are coated on medical devices for prophylactic administration.
13. The composition of embodiment 12, wherein said medical devices are implants or catheters.
14. A method of treating an infection comprising topically applying in infected areas an effective amount of a toxin-neutralizing antimicrobial hydrogel impregnated with toxinabsorbing nanoparticles.
15. The method of embodiment 14, wherein said toxin-neutralizing antimicrobial hydrogel comprises poly(ethylene glycol) dimethacrylate (PEGDMA).
16. The method of embodiment 14, wherein said nanoparticles comprise a core material coated with red blood cell membranes.
17. The method of embodiment 14, wherein said toxin-neutralizing antimicrobial hydrogel further comprises antibiotics.
18. A method of preserving therapeutic nanoparticle functionalities comprising formulating a toxin-neutralizing antimicrobial hydrogel impregnated with toxin-absorbing nanoparticles.
19. The method of embodiment 18, wherein said toxin-neutralizing antimicrobial hydrogel comprises poly(ethylene glycol) dimethacrylate (PEGDMA).
20. The method of embodiment 18, wherein said nanoparticle comprises a core material coated with red blood cell membranes.

REFERENCES

1a. Siddiqui, A. R. & Bernstein, J. M. Chronic wound infection: Facts and controversies. *Clin Dermatol* 28, 519-526 (2010).

2a. Salome Veiga, A. & Schneider, J. P. Antimicrobial hydrogels for the treatment of infection. *Biopolymers* 100, 637-644 (2013).

3a. Woo, G. L., Mittelman, M. W. & Santerre, J. P. Synthesis and characterization of a novel biodegradable antimicrobial polymer. *Biomaterials* 21, 1235-1246 (2000).

4a. Campbell, A. A. et al. Development, characterization, and anti-microbial efficacy of hydroxyapatite-chlorhexidine coatings produced by surface-induced mineralization. *J Biomed Mater Res* 53, 400-407 (2000).

5a. Dinges, M. M., Orwin, P. M. & Schlievert, P. M. Exotoxins of *Staphylococcus aureus*. *Clinical microbiology reviews* 13, 16-34, table of contents (2000).

6a. Unal, N. et al. Panton-Valentine leukocidin and some exotoxins of *Staphylococcus aureus* and antimicrobial susceptibility profiles of staphylococci isolated from milks of small ruminants. *Tropical animal health and production* 44, 573-579 (2012).

7a. Stassen, M. et al. The streptococcal exotoxin streptolysin 0 activates mast cells to produce tumor necrosis factor alpha by p38 mitogen-activated protein kinase- and protein kinase C-dependent pathways. *Infection and immunity* 71, 6171-6177 (2003).

8a. Hu, C. M., Fang, R. H., Copp, J., Luk, B. T. & Zhang, L. A biomimetic nanosponge that absorbs pore-forming toxins. *Nature nanotechnology* 8, 336-340 (2013).

9a. Hu, C. M., Fang, R. H., Luk, B. T. & Zhang, L. Nanoparticle-detained toxins for safe and effective vaccination. *Nature nanotechnology* (2013).

F. Example

Hydrogel Retaining Toxin-Absorbing Nanosponges for Local Treatment of Methicillin-Resistant *Staphylococcus aureus* Infection Targeting virulence factors such as bacterial toxins represents an attractive antimicrobial approach with potential advantages of expanding the repertoire of bacterial targets, preserving the host endogenous microbiome, and lowering selective pressure for resistance development.[1, 2] Among various toxins, pore-forming toxins (PFTs) are the most common class of bacterial protein toxins and constitute important bacterial virulence factors.[3] These toxins disrupt cells by forming pores on cellular membranes and altering their permeability for bioactivity.[4] However, the majority of current toxin targeting strategies, such as antisera,[5] monoclonal antibodies,[6, 7] small-molecule inhibitors,[8, 9] and molecularly imprinted polymers,[10] relies primarily on structure-specific epitopic binding and custom synthesis is required to match specific toxins. As a result, the enormous diversity of PFTs presents a serious challenge to devise an effective detoxification platform against bacterial infections. To address this challenge, a unique red blood cell (RBC) membrane-coated nanoparticle system has been recently developed by wrapping intact RBC membrane onto polymeric nanoparticle, leading to a broadly applicable toxin-absorbing "nanosponge" for detoxification applications.[11, 12] Different from existing detoxification strategies, the nanosponge targets the membrane-disrupting mechanism common to PFTs; thereby offering an all-purpose toxin decoy strategy to absorb various types of PFTs regardless of their molecular structures.[12]

Meanwhile, on the front of nanotechnology development, therapeutic nanoparticles are increasingly combined with other biomaterials to form hybrid nanostructures for improved therapeutic index. Particularly, loading nanoparticles into hydrogels have received much attention.[13] Hydrogels are hydrophilic 3D polymer networks with extensive uses in tissue engineering and drug delivery. With appropriate compositions, hydrogels can not only preserve the structural integrity and the functionalities of the contained nanoparticles but also offer additional engineering flexibility to improve the therapeutic efficacy. For example, biopolymers were linked together by selective adsorption to nanoparticles, forming self-assembled hydrogels with shear-thinning and self-healing properties.[14] Modifying hydrogel composition has also allowed for controllable nanoparticle release and tunable viscoelasticity suitable for topical applications.[15, 16] Hydrogels made from responsive polymer matrices have also been attempted to load nanoparticles for controlled releases triggered by environmental cues such as pH, ionic strength, and temperature.[17, 18] Recently, polymeric nanoparticles were also loaded into liver lobule-mimicking hydrogel for toxin entrapment.[19] Inspired by the numerous advantages of hydrogels in retaining nanoparticles and enhancing their properties, herein, we report on an advanced hybrid nanoformulation that integrates toxin nanosponge with hydrogel for local treatment of bacterial infection.

Among various bacterial pathogens, *Staphylococcus aureus* (*S. aureus*) is a prominent Gram-positive bacterium and the leading cause for a vast range of human skin and wound infections.[20,21] Over the past a few decades, *S. aureus* has experienced several waves of antibiotic resistance and now displays broad resistance to the entire beta-lactam class of antibiotics, including penicillins, cephalosporins, and carbapenems.[22] To keep up the pace of antibiotic resistance, new antibiotics including vancomycine, linezolid, tedezolid, daptomycin, ceftaroline, and tigecycliine have been developed and introduced in recent years. However, emergence of resistant *S. aureus* strains, especially toward vancomycin, has significantly increased.[23] Currently, virulent strains of methicillin-resistant *S. aureus* (MRSA) have become increasingly prevalent, imposing a paramount clinical challenge that threatens public health.[24-26] Collectively, these facts underscore the undisputed and urgent need to develop new and effective therapeutic approaches for MRSA treatment.

Notably, MRSA infections are commonly localized to skin and soft tissues.[27] In these infections, a critical element of virulence results from a diverse arsenal of PFTs secreted by the bacteria, which attack the host cells.[28] These distinctive features of MRSA infections make the nanosponge-hydrogel hybrid formulation an attractive treatment strategy against such infections (FIG. 7A). The hydrogel composition can be optimized to effectively retain nanosponges within its matrix without compromising toxin transport for neutralization. In the study, we confirm the in vitro and in vivo toxin neutralization capabilities of the nanosponge-hydrogel formulation. When injected in situ, the hydrogel can effectively retain nanosponges at the injection sites, a property favoring toxin absorption. In a subcutaneous MRSA mouse model, the hybrid formulation shows significant anti-virulence therapeutic efficacy, evidenced by the markedly reduced MRSA skin lesion development. Overall, we demonstrate the potential of the nanosponge-loaded hydrogel as a new and effective detoxification strategy for the treatment of localized MRSA infection.

The preparation of nanosponge-loaded hydrogel (denoted "NS-gel") was divided into two steps. In the first step, we prepared nanosponges by mechanically extruding purified mouse RBC membrane with 100 nm of poly(lactic-co-glycolic acid) (PLGA) polymeric cores. Membrane coating was confirmed with transmission electron microscope (TEM).[11, 29] In the second step, we mixed pre-formed nanosponges with acrylamide as the monomer and poly (ethylene glycol) dimethacrylate (PEGDMA) as the crosslinker. Hydrogelation was initiated by adding ammonium persulfate and tetramethylethylenediamine (TEMED), and allowed to proceed for 12 h at room temperature.[16]

The hydrogel composition was optimized for effective nanosponge retention while maintaining a low viscosity suitable for injection. To this end, we first labeled the nanosponges with 1,1'-dioctadecyl-3,3,3',3' tetramethylindodicarbocyanine, 4-chlorobenzenesulfonate salt (DiD) (excitation/emission=644 nm/655 nm), a hydrophobic fluorophore with negligible leakage from PLGA polymer matrix.[11, 30] Then we fixed the concentrations of nanosponges, acrylamide, ammonium persulfate, and TEMED as 2 mg/mL (PLGA content), 40 mg/mL, 1 mg/mL and 1 µL/mL, respectively, but varied PEGDMA concentrations and accordingly examined the nanosponge release from the corresponding hydrogels. As shown in FIG. 7B, the accumulated release of nanosponge over 24 h decreased abruptly from approximately 53% at 0.5 (w/v) % crosslinker concentration to no more than 5% at 0.6 (w/v) %, suggesting that the latter PEGDMA concentration was adequate in forming a hydrogel for effectively retaining nanosponges. This crosslinker concentration was used to prepare NS-gel for the following studies.

The NS-gel was further characterized with dynamic rheological measurements of the storage modulus (G') and the loss modulus (G") as a function of frequency (FIG. 7C). In the study, G' exceeded G" over the entire frequency range, a clear viscoelastic behavior indicating the formation of a hydrogel network.[16] In addition, G' and G" values measured from NS-gel were close to those measured from the empty hydrogel (without nanosponges), suggesting a negligible effect of the loaded nanosponges on the gel's rheological characteristics. We then freeze-dried the NS-gel and observed its structure under scanning electron microscope (SEM). The sample showed characteristic porous sponge-like structures with some irregular lamellar features (FIG. 7D). At a higher magnification, nanosponge particles with a diameter of approximately 100 nm embedded within the hydrogel were also observed (FIG. 7D, insert).

We then compared the ability of the NS-gel in absorbing α-toxin to that of the empty gel. When α-toxin solution was added to the empty gel of an equal volume, a gradual decrease of toxin concentration was observed within the first 1 h of incubation until it reached approximately 50% of the original concentration (FIG. 7E). No further decrease of the toxin concentration was observed with prolonged incubation time, suggesting a slow diffusion process of α-toxin into the hydrogel network until equilibrium was reached. In contrast, when α-toxin solution was incubated with the NS-gel, a sharp decrease of toxin concentration was observed within the first 30 min of incubation. After 1 h, no more than 5% of the initial toxin was left in the solution. Such significantly increased ability of the NS-gel in absorbing α-toxin suggests its potential for detoxification applications.

Figure 8A:
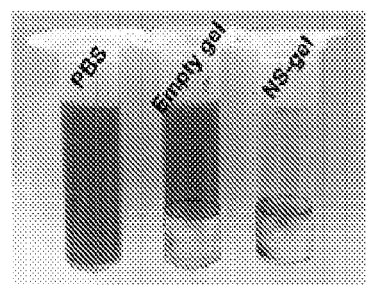
FIGS. 8A-8D illustrate in vitro toxin neutralization.
Figure 8B:
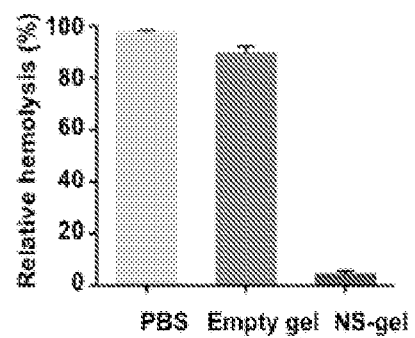
Figure 8C:
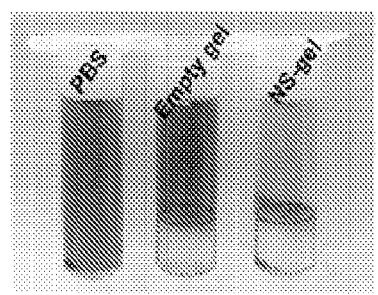
Figure 8D:
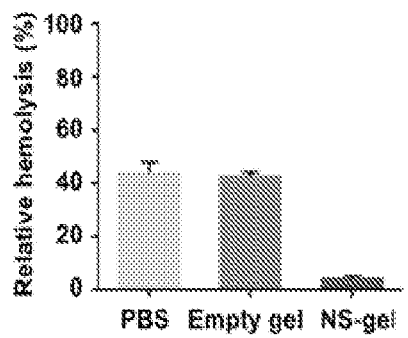

To test the ability of the NS-gel to neutralize PFTs, we used a hemolytic assay where α-toxin was mixed with the NS-gel and then added to purified mouse RBCs.[12] PBS and the empty gel were tested in parallel as controls. As shown in FIG. 8A, NS-gel sample showed a clear supernatant, suggesting the RBCs were undamaged. In contrast, noticeable differences were observed with other samples, which showed significant RBC lysis. The degree of hemolysis was quantified by measuring the absorbance of the released hemoglobin in the supernatant at 540 nm (FIG. 8B). The capability of the NS-gel to absorb toxins secreted by MRSA bacteria was further examined by mixing the NS-gel with MRSA culture medium known to contain multiple virulent PFTs.[31, 32] As shown in FIGS. 8C and D, a similar reduction of RBC hemolysis by the NS-gel was observed as compared to the control groups, demonstrating the NS-gel's applicability in neutralizing multiple types of RBC membrane-targeted PFTs secreted by the bacteria.

Next, we evaluated the retention of the nanosponges by the hydrogel upon in vivo administration. In the study, we formulated the NS-gel with DiD-labeled nanosponges and injected the NS-gel subcutaneously on the left flank of the mice. As a control, the same amount of nanosponges suspended in PBS was injected to the right flank of the same mice. For both groups, the whole body imaging revealed the confinement of fluorescence at the injection sites within 48 h (FIG. 9A). However, a more rapid decay of fluorescence intensity was observed at the site injected with nanosponges suspended in PBS, indicating a faster loss of nanoparticles through diffusion to surrounding tissues. Quantification of the fluorescence intensity showed that nearly 80% of the free nanosponges diffused away from the injection site within 2 h. In contrast, the NS-gel had negligible loss of the nanosponge payloads within the initial 2 h and only lost approximately 20% of the total nanosponge during the 48 h testing period (FIG. 9B). This study, together with the previous in vitro nanosponge release results (FIG. 7B), clearly demonstrated the prolonged retention of the nanosponges conferred by the hydrogel formulation. These results further indicate that the NS-gel could be a competent formulation for the treatment of local bacterial infection, in which the pathogens reside on a localized area of a tissue.

The ability of the NS-gel to neutralize α-toxin was further examined in vivo by subcutaneous injection of α-toxin (50 μL at a concentration of 40 μg/mL in PBS) immediately followed by injecting empty gel or NS-gel (100 μL), respectively, beneath the right flank skin of mice. For the mice treated with empty gel, 72 h after the injection obvious skin lesions were induced with demonstrable oedema and inflammation (FIG. 10A). Closer examination of the skin tissue showed typical indications of toxin-induced damages, including necrosis, apoptosis and inflammatory infiltrate of neutrophils with dermal oedema (FIG. 10B).[12, 33] Moreover, the toxin damaged the underlying muscle tissue, as indicated by interfibril oedema, tears on muscles fibres and a significant number of extravasating neutrophils from the surrounding vasculature (FIG. 10C).[12] However, mice treated with NS-gel showed no observable damage on the skin (FIG. 10D). The tissue samples showed normal epithelial structures in skin histology (FIG. 10E) and intact fibrous structures with no visible infiltrate in muscle histology (FIG. 10F).

Figure 11:
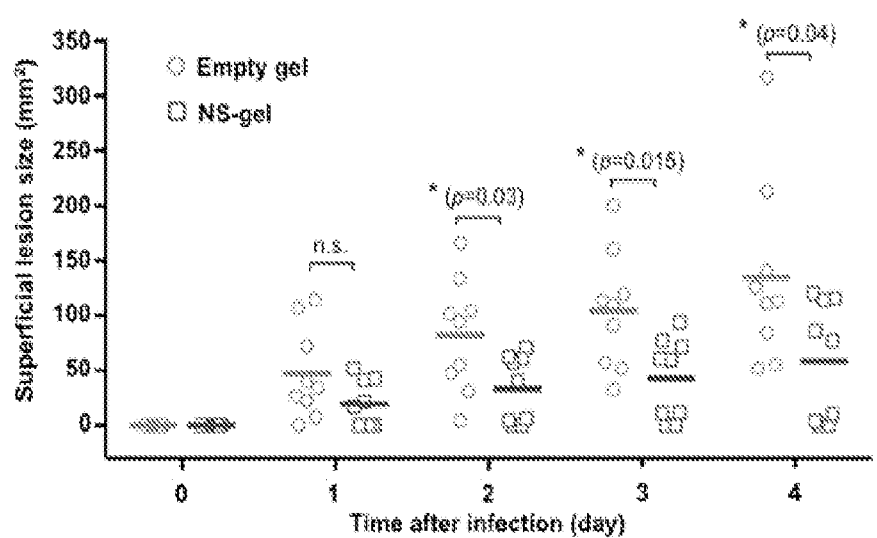
FIG. 11 illustrates in vivo treatment of MRSA infection. $1\times10^9$ CFU of MRSA 252 was mixed with 0.2 mL of 2 mg/mL NS-gel or empty gels, followed by subcutaneous injection under the loose skin on the back of the mice (n=9 per group). Skin lesions were monitored and photographed on day 1 to 4 after the injections and the lesion sizes were measured. Bars represent median values. *P<0.05, n.s.: not significant.

Finally, we proceeded to examine the in vivo anti-MRSA efficacy of the NS-gel. To establish a subcutaneous MRSA infection model, we injected $1 \times 10^9$ CFU MRSA bacteria under the flank skin of each ICR mouse.[33] The infected mice were randomly divided into two groups (n=9) and then injected at the infection sites with the NS-gel and empty gel, respectively. Herein, to evaluate therapeutic efficacy, we chose to compare MRSA-induced skin lesion size, a common index reflecting the severity of the infection.[33-35] After 24 h, mice in both groups developed visible skin lesions but the size difference was non-significant (FIG. 11). At 48 h, the lesion sizes increased in both groups; however, the mice treated with the NS-gel showed a significantly smaller skin lesion when compared to those treated with the empty gel. At 72 h and 96 h, the lesion sizes continued to increase in both groups as the infection continued to progress. The lesion size of the NS-gel treated group remained significantly smaller than that of the group treated with the empty-gel. This superior efficacy observed with the NS-gel demonstrates its potential as a local treatment strategy effective against MRSA infection.

Previously, we reported that RBC-membrane coated nanoparticles (i.e., nanosponges) were effective in neutralizing PFTs including α-toxin, streptolysin-O, and melittin.[12] The current study took this platform one important step further by directly demonstrating its effectiveness in treating MRSA infection in a mouse model. This advancement is enabled by the combined advantages of the nanosponges and the hydrogel: while the nanosponges absorbing and diverting PFTs away from the cellular targets, the hydrogel retained nanosponges at the infection sites, promoting localized toxin neutralization for better therapeutic efficacy. The observed anti-virulence efficacy reflects the synergy of such combination. With improved versatility and functionality, such advanced hybrid materials are expected to offer a practical and reliable formulation that facilitates downstream preclinical and clinical tests.

The rapid technological developments in nanotechnology and biomaterials provide a promising potential for engineering advanced materials through hybridization.[36, 37] On one hand, nanoparticle platforms are gaining an increasing attention for broad-spectrum toxin neutralization.[38, 39] For example, we have recently extended the nanosponges to neutralize other chemical and biological molecules that target RBCs such as pathological antibodies driving prevalent autoimmune diseases.[30] Meanwhile, cell membrane coating technology has also been increasingly explored to functionalize various types of nanoparticles, including those made from gold,[40, 41] silica,[42] and gelatin,[43] opening unprecedented capability to harness natural functionalities for innovative therapeutics. On the other hand, the technological advance has also led to the development of hydrogels featuring highly interactive, integrative, and biocompatible characteristics for increasingly advanced drug delivery and tissue engineering applications.[44-46] Integrating hydrogel with nano sponges, or cell membrane coated nanoparticles in general, is anticipated to result in advanced materials that harness the advantages of each building material. We believe that this design strategy will open unique opportunities for a wide range of therapeutic applications.

In summary, we developed an advanced hybrid material that integrates a unique toxin-absorbing nanosponge with hydrogel for anti-virulence treatment of local bacterial infection. The nanosponges were made by wrapping intact RBC membrane onto polymeric nanoparticles made from PLGA, followed by loading into hydrogels. The hydrogel composition was optimized to effectively retain nanosponges within its matrix without compromising toxin transport for neutralization. Following subcutaneous injection to mice, nanosponges were effectively retained at the injection sites. In a MRSA subcutaneous mouse model, mice treated with the nanosponge-hydrogel hybrid showed markedly reduced MRSA skin lesion development. These results collectively indicate that the nanosponge-hydrogel hybrid formulation represents a new and effective detoxification strategy for the treatment of localized bacterial infection.

Experimental Section

Preparation of Nanosponges.

The nanosponge was prepared following previously described methods.[11, 12] Briefly, poly($_{DL}$-lactide-co-glycolide) (PLGA) polymeric nanoparticles with a diameter of about 100 nm were prepared with 0.67 dL/g of carboxy-terminated 50:50 PLGA polymer (LACTEL Absorbable Polymers) through a nanoprecipitation process. Specifically, the PLGA polymer was first dissolved in acetone at a concentration of 10 mg/mL. Then 1 mL of the solution was added to 3 mL of deionized water. The mixture was then stirred in open air for 1 h and placed in vacuum for another 3 h. The resulting nanoparticle solution was filtered using an Amicon Ultra-4 centrifugal filter with a molecular weight cutoff of 10 kDa (Millipore). To prepare fluorescently labeled nanosponges, 0.1 wt % 1,1'-dioctadecyl-3,3,3',3'-tetramethylindodicarbocyanine perchlorate (DiD; excitation/emission=644/665 nm; Life Technologies) was added to the polymers prior to PLGA nanoparticle synthesis. RBC membrane coating was then completed by fusing RBC membrane-derived vesicles with PLGA nanoparticles via sonication using an FS30D bath sonicator at a frequency of 42 kHz and a power of 100 W for 2 min Dynamic light scattering (DLS) measurements on the resulting nanosponges (Malvern ZEN 3600 Zetasizer) showed an average hydrodynamic diameter of about 100 nm and 115 nm before and after the membrane coating process, respectively. The core-shell structure of the nanosponge was confirmed by using transmission electron microscope (TEM, FEI 200 kV Sphera microscope).

Preparation of Nanosponge-Loaded Hydrogel (NS-Gel).

To prepare hydrogel, acrylamide (used as the monomer), poly(ethylene glycol) dimethacrylate (PEGDMA, used as the cross-linker), tetramethylethylene diamine (TEMED), and ammonium persulfate (both used as initiators) were purchased from Sigma-Aldrich. For the empty hydrogel, the final concentrations of acrylamide, ammonium persulfate and TEMED were kept constant at 40 mg/mL, 1 mg/mL, and 1 µL/mL, respectively, while PEGDMA concentration was tested in the range of 0-1% w/w. The liquid mixture was vortexed for 1 min and then placed in a vacuum chamber at room temperature for 2 h to allow complete gelation to occur. For NS-gel, nanosponges with a final concentration of 2 mg/mL were mixed the aforementioned chemicals followed by gelation.

To measure nanosponge release rate from the hydrogel, DiD dye-labeled nanosponges were used to prepare NS-gels at different PEGDMA concentrations. Then 0.5 mL NS-gel was submerged into 50 mL PBS. The mixture was incubated at 37° C. for 24 h and the DiD signal from the supernatant was measured. The rheological analysis was carried out at 37±0.1° C. on a strain-controlled AR-G2 rheometer with 22 mm diameter parallel-plate geometry (TA Instruments Inc., New Castle, Del.). Oscillatory rheological measurements were performed in the linear viscoelastic regime. The strain was kept at 0.1% and a dynamic frequency sweep from 0.1 to 10 rad/s was conducted to measure the storage modulus G' and loss modulus G". To study hydrogel morphology, NS-gel was lyophilized and the flakes of the gel were placed on a silicon wafer. The samples were coated with iridium and then examined with scanning electron microscope (SEM). Absorption of α-toxin by NS-gel was examined by incubating 2 mL α-toxin (2 µg/mL) with 0.5 mL NS-gel at 37° C. for 24 h. Empty hydrogel was used as a control group. At 4, 8, and 24 h time points, α-toxin concentration in the supernatants was quantified with ELISA (R&D Systems, Inc., Minneapolis, Minn.).

In Vitro α-Toxin Neutralization Study.

To evaluate α-toxin neutralization by NS-gel in vitro, a hemolytic assay was conducted. Briefly, 3 µL of α-toxin solution (1 mg/mL) was mixed with 0.5 mL NS-gel, empty hydrogel, and PBS, respectively. Then 1 mL of 5% purified mouse RBCs was added to the top of each sample, followed by incubation at 37° C. for 1 h. Then the samples were carefully centrifuged. The extent of RBC lysis was quantified by measuring the absorption of the supernatants at 540 nm. To neutralize toxins in bacterial supernatant, MRSA culture (from an overnight culture of 1×10$^9$ CFU/mL of MRSA 252) was used to dissolve the chemicals for the hydrogel preparation. All experiments were performed in triplicate.

Live Whole-Body Imaging of Mice to Study Nanosponge Retention.

Prior to the study, the back of the mice (6 week-old male ICR mice from Charles River Laboratories, n=3) was carefully shaved. Then 50 µL DiD labeled NS-gel was injected subcutaneously to the left flanks of the mice. As a control, nanosponges suspended in PBS (2 mg/mL, 50 µL) were injected subcutaneously to the right flanks the same mice. At the designated time points (0, 6, 24, and 48 h), mice were anesthetized with isoflurane and imaged with a Xenogen IVIS 200 system. Fluorescence intensities were quantified and normalized across the time points. Heat maps were overlaid on bright field images.

In Vivo α-Toxin Neutralization Study.

Neutralization of α-toxin by the NS-gel was conducted by subcutaneously injecting 50 µL of 40 µg/mL of α-toxin solution into the flank region of 6 week-old male ICR mice (Charles River Laboratories, n=3), immediately followed by injecting 100 µL empty gel or NS-gel into the same region. After 72 h the mice were imaged. Then the mice were sacrificed and the skin and muscle samples were removed. The tissues were frozen, cut, and then stained with hematoxylin and eosin (H&E) for histological analysis.

In Vivo Detoxification Efficacy Against Localized MRSA Infection.

To evaluate in vivo detoxification efficacy of the NS-gel against MRSA infection, a MRSA subcutaneous infection mouse model was used. Briefly, prior to the study, the back of 18 ICR mice (6 week-old male, Charles River Laboratories) was carefully shaved. Then $1 \times 10^9$ CFU of MRSA 252 suspended in 50 µL PBS was injected subcutaneously into the flank region. Then the mice were randomly divided into two groups (n=9). For the treatment group, 0.2 mL NS-gel was injected into the infection region. For the control group, the empty gel instead of NS-gel was injected. The lesion of each mouse was carefully monitored. The lesion was photographed and the lesion size was measured from the photography by using Image J.

REFERENCES

[1] A. E. Clatworthy, E. Pierson, D. T. Hung, *Nat. Chem. Biol.* 2007, 3, 541.
[2] D. A. Rasko, V. Sperandio, *Nat. Rev. Drug Discov.* 2010, 9, 117.
[3] F. C. O. Los, T. M. Randis, R. V. Aroian, A. J. Ratner, *Microbiol. Mol. Biol. Rev.* 2013, 77, 173.
[4] R. J. C. Gilbert, *Cell. Mol. Life Sci.* 2002, 59, 832.
[5] D. G. Beghini, S. Hernandez-Oliveira, L. Rodrigues-Simioni, J. C. Novello, S. Hyslop, S. Marangoni, *Toxicon* 2004, 44, 141.
[6] L. W. Cheng, T. D. Henderson, II, S. Patfield, L. H. Stanker, X. He, *Toxins* 2013, 5, 1845.
[7] V. Oganesyan, L. Peng, M. M. Damschroder, L. Cheng, A. Sadowska, C. Tkaczyk, B. R. Sellman, H. Wu, W. F. Dall'Acqua, *J. Biol. Chem.* 2014, 289, 29874.
[8] D. T. Hung, E. A. Shakhnovich, E. Pierson, J. J. Mekalanos, *Science* 2005, 310, 670.
[9] C. C. McCormick, A. R. Caballero, C. L. Balzli, A. Tang, R. J. O'Callaghan, *Invest. Ophthalmol. Vis. Sci.* 2009, 50, 2848.
[10] Y. Hoshino, H. Koide, K. Furuya, W. W. Haberaecker, III, S.-H. Lee, T. Kodama, H. Kanazawa, N. Oku, K. J. Shea, *Proc. Natl. Acad. Sci. USA* 2012, 109, 33.
[11] C.-M. J. Hu, L. Zhang, S. Aryal, C. Cheung, R. H. Fang, L. Zhang, *Proc. Natl. Acad. Sci. USA* 2011, 108, 10980.
[12] C.-M. J. Hu, R. H. Fang, J. Copp, B. T. Luk, L. Zhang, *Nat. Nanotechnol.* 2013, 8, 336.
[13] P. Schexnailder, G. Schmidt, *Colloid. Polym. Sci.* 2009, 287, 1.
[14] E. A. Appel, M. W. Tibbitt, M. J. Webber, B. A. Mattix, O. Veiseh, R. Langer, *Nat. Commun.* 2015, 6, article number 6295.
[15] Y. Sekine, Y. Moritani, T. Ikeda-Fukazawa, Y. Sasaki, K. Akiyoshi, *Adv. Healthc. Mater.* 2012, 1, 722.
[16] W. Gao, D. Vecchio, J. Li, J. Zhu, Q. Zhang, V. Fu, J. Li, S. Thamphiwatana, D. Lu, L. Zhang, *ACS Nano* 2014, 8, 2900.
[17] R. M. K. Ramanan, P. Chellamuthu, L. P. Tang, K. T. Nguyen, *Biotechnol. Prog.* 2006, 22, 118.
[18] Y. Xiang, D. Chen, *Eur. Polym. J.* 2007, 43, 4178.
[19] M. Gou, X. Qu, W. Zhu, M. Xiang, J. Yang, K. Zhang, Y. Wei, S. Chen, *Nat. Commun.* 2014, 5, article number 3774.
[20] M. J. Kuehnert, D. Kruszon-Moran, H. A. Hill, G. McQuillan, S. K. McAllister, G. Fosheim, L. K. McDougal, J. Chaitram, B. Jensen, S. K. Fridkin, G. Killgore, F. C. Tenover, *J. Infect. Dis.* 2006, 193, 172.
[21] A. J. Singer, D. A. Talan, *New Engl. J. Med.* 2014, 370, 1039.
[22] H. F. Chambers, F. R. DeLeo, *Nat. Rev. Microbiol.* 2009, 7, 629.
[23] L. M. Weigel, D. B. Clewell, S. R. Gill, N. C. Clark, L. K. McDougal, S. E. Flannagan, J. F. Kolonay, J. Shetty, G. E. Killgore, F. C. Tenover, *Science* 2003, 302, 1569.
[24] K. Hiramatsu, N. Aritaka, H. Hanaki, S. Kawasaki, Y. Hosoda, S. Hori, Y. Fukuchi, I. Kobayashi, *Lancet* 1997, 350, 1670.
[25] R. M. Klevens, J. R. Edwards, F. C. Tenover, L. C. McDonald, T. Horan, R. Gaynes, S. Natl Nosocomial Infections, *Clin. Infect. Dis.* 2006, 42, 389.
[26] M. McKenna, *Nature* 2012, 482, 23.
[27] R. J. Gordon, F. D. Lowy, *Clin. Infect. Dis.* 2008, 46, 5350.
[28] R. J. Gorwitz, *J. Infect. Dis.* 2008, 197, 179.
[29] C.-M. J. Hu, L. Zhang, *Nano Today* 2014, 9, 401.
[30] J. A. Copp, R. H. Fang, B. T. Luk, C.-M. J. Hu, W. Gao, K. Zhang, L. Zhang, *Proc. Natl. Acad. Sci. USA* 2014, 111, 13481.
[31] R. Wang, K. R. Braughton, D. Kretschmer, T.-H. L. Bach, S. Y. Queck, M. Li, A. D. Kennedy, D. W. Dorward, S. J. Klebanoff, A. Peschel, F. R. DeLeo, M. Otto, *Nat. Med.* 2007, 13, 1510.
[32] M. Li, G. Y. C. Cheung, J. Hu, D. Wang, H.-S. Joo, F. R. DeLeo, M. Otto, *J. Infect. Dis.* 2010, 202, 1866.
[33] M. R. Yeaman, S. G. Filler, S. Chaili, K. Barr, H. Wang, D. Kupferwasser, J. P. Hennessey, Y. Fu, C. S. Schmidt, J. E. Edwards, Jr., Y. Q. Xiong, A. S. Ibrahim, *Proc. Natl. Acad. Sci. USA* 2014, 111, E5555.
[34] Y. Guo, R. I. Ramos, J. S. Cho, N. P. Donegan, A. L. Cheung, L. S. Miller, *Antimicrob. Agents Chemother.* 2013, 57, 855.
[35] D. Das, P. M. Tulkens, P. Mehra, E. Fang, P. Prokocimer, *Clin. Infect. Dis.* 2014, 58, S51.
[36] J. Kopecek, J. Yang, *Angew. Chem. Int. Ed. Engl.* 2012, 51, 7396.
[37] K. Kanie, R. Kurimoto, M. Ebara, N. Idota, Y. Narita, H. Honda, R. Kato, J. *Tissue Eng. Regen. Med.* 2014, 8, 220.
[38] V. Forster, R. D. Signorell, M. Roveri, J.-C. Leroux, *Sci. Transl. Med.* 2014, 6, article number 258ra141.
[39] A. Weisman, Y. A. Chen, Y. Hoshino, H. Zhang, K. Shea, *Biomacromolecules* 2014, 15, 3290.
[40] W. Gao, C.-M. J. Hu, R. H. Fang, B. T. Luk, J. Su, L. Zhang, *Adv. Mater.* 2013, 25, 3549.
[41] J.-G. Piao, L. Wang, F. Gao, Y.-Z. You, Y. Xiong, L. Yang, *ACS Nano* 2014, 8, 10414.
[42] A. Parodi, N. Quattrocchi, A. L. van de Ven, C. Chiappini, M. Evangelopoulos, J. O. Martinez, B. S. Brown, S. Z. Khaled, I. K. Yazdi, M. Vittoria Enzo, L. Isenhart, M. Ferrari, E. Tasciotti, *Nat. Nanotechnol.* 2013, 8, 61.
[43] L.-L. Li, J.-H. Xu, G.-B. Qi, X. Zhao, F. Yu, H. Wang, *ACS Nano* 2014, 8, 4975.
[44] J. A. Burdick, W. L. Murphy, *Nat. Commun.* 2012, 3, article number 1269.
[45] Y. Li, J. Rodrigues, H. Tomas, *Chem. Soc. Rev.* 2012, 41, 2193.
[46] A. S. Hoffman, *Adv. Drug Del. Rev.* 2012, 64, 18.

The invention claimed is:

1. A method for decreasing or neutralizing the effect of a toxin, or for treating an infection by a microbe that produces a toxin, in a subject, which method comprises administering, to a subject in need, or to cells of said subject, an effective amount of a composition comprising a polymeric hydrogel impregnated with a toxin-absorbing or binding nanoparticle, wherein said nanoparticle comprises a) an inner core comprising a non-cellular material, and b) an outer surface comprising a cellular membrane configured for absorbing or binding said toxin, wherein said cellular membrane of said nanoparticle comprises a plasma membrane or an intracellular membrane.

2. The method of claim 1, wherein the subject is a mammal.

3. The method of claim 2, wherein the mammal is a human.

4. The method of claim 2, wherein the mammal is a non-human mammal.

5. The method of claim 1, which is used for decreasing the effect of a toxin in the subject.

6. The method of claim 1, which is used for neutralizing the effect of a toxin in the subject.

7. The method of claim 1, which is used for treating an infection by a microbe that produces a toxin in the subject.

8. The method of claim 1, wherein the nanoparticle in the composition substantially lacks immunogenicity to the subject.

9. The method of claim 8, wherein the cellular membrane is derived from a red blood cell from the same species of the subject.

10. The method of claim 9, wherein the subject is a human and the cellular membrane is derived from a human red blood cell.

11. The method of claim 10, wherein the cellular membrane is derived from a red blood cell of the human to be treated.

12. The method of claim 1, wherein the composition is administered to the subject using a medicament delivery system or a medical device.

13. The method of claim 1, wherein the composition is administered to the subject via rectal, nasal, topical, ocular, intramuscular, intraperitoneal, or subcutaneous route of administration.

14. The method of claim 13, wherein the composition is administered to the subject via topical route of administration.

15. The method of claim 1, wherein the hydrogel in the composition comprises poly(ethylene glycol) dimethacrylate (PEGDMA).

16. The method of claim 1, wherein the cellular membrane of the nanoparticle in the composition comprises a plasma membrane derived from a red blood cell.

17. The method of claim 16, which further comprises administering an antibiotic to the subject.

18. The method of claim 17, wherein the antibiotic is comprised in the composition.

19. The method of claim 18, wherein the antibiotic is comprised in a releasable cargo of the nanoparticle in the composition.

20. The method of claim 1, wherein the polymeric hydrogel comprises a material selected from the group consisting of poly(ethylene glycol) dimethacrylate (PEGDMA), silicone, gelatin, chitosan, alginate, polyester, poly(vinyl alcohol) and polyacrylamide, polyethylene oxide, polyvinyl alcohol, polyacrylamidomethylpropanesulfonate, polyacrylic acid, a salt of acrylic acid, agarose, methylcellulose, hyaluronan, and copolymers thereof.

21. The method of claim 1, wherein, during use, the polymeric hydrogel comprises at least about 1% water (w/w).

22. The method of claim 1, wherein the polymeric hydrogel possess a degree of flexibility suitable to be applied to a tissue or an organ.

23. The method of claim 1, wherein the inner core of the nanoparticle comprises a polymeric particle core, a silica particle core, or a metal particle core.

24. The method of claim 1, wherein the inner core of the nanoparticle comprises a biocompatible or a synthetic material selected from the group consisting of poly(lactic-c-glycolic acid) (PLGA), polylactic acid (PLA), polyglycolic acid (PGA), polycaprolactone (PCL), polylysine, and polyglutamic acid.

25. The method of claim 1, wherein the inner core of the nanoparticle supports the outer surface of the nanoparticle.

26. The method of claim 1, wherein the cellular membrane of the nanoparticle comprises a plasma membrane.

27. The method of claim 1, wherein the nanoparticle has a diameter from about 10 nm to about 10 μm.

28. The method of claim 1, wherein the nanoparticle substantially lacks constituents of the cell from which the cellular membrane is derived.

29. The method of claim 1, wherein the nanoparticle substantially maintains natural structural integrity or activity of the cellular membrane or the constituents of the cellular membrane.

30. The method of claim 1, wherein the nanoparticle is biocompatible or biodegradable.

31. The method of claim 1, wherein the inner core of the nanoparticle comprises PLGA and the outer surface of the nanoparticle comprises a plasma membrane derived from a red blood cell.

32. The method of claim 1, wherein the polymeric hydrogel comprises hydrated polymeric networks that are either physically or covalently crosslinked with each other and/or with the nanoparticle(s).

33. The method of claim 1, wherein the nanoparticle further comprises a therapeutic agent, a prophylactic agent, a diagnostic or marker agent, a prognostic agent, an isolation agent, a monitoring agent, or a combination thereof.

* * * * *